US009642381B2

(12) United States Patent
Ley et al.

(10) Patent No.: US 9,642,381 B2
(45) Date of Patent: May 9, 2017

(54) ORALLY CONSUMABLE FORMULATIONS COMPRISING CERTAIN SWEET-TASTING TRITERPENES AND TRITERPENE GLYCOSIDES

(75) Inventors: Jakob Ley, Holzminden (DE); Katharina Reichelt, Holzminden (DE); Katja Obst, Holzminden (DE); Ludger Wessjohann, Halle (DE); Sabine Wessjohann, Halle (DE); Tran Van Sung, Hanoi (VN); The Anh Nguyen, Hanoi (VN); Ngo Van Trai, Hanoi (VN)

(73) Assignee: Symrise AG, Holzminden (DE)

( * ) Notice: Subject to any disclaimer, the term of this patent is extended or adjusted under 35 U.S.C. 154(b) by 395 days.

(21) Appl. No.: 14/122,550

(22) PCT Filed: Jun. 1, 2012

(86) PCT No.: PCT/EP2012/060344
§ 371 (c)(1),
(2), (4) Date: Mar. 5, 2014

(87) PCT Pub. No.: WO2012/164062
PCT Pub. Date: Dec. 6, 2012

(65) Prior Publication Data
US 2014/0170083 A1    Jun. 19, 2014

Related U.S. Application Data

(60) Provisional application No. 61/492,073, filed on Jun. 1, 2011.

(30) Foreign Application Priority Data

Jun. 1, 2011   (EP) ..................................... 11168468

(51) Int. Cl.
| A23L 1/236 | (2006.01) |
| A61K 8/63 | (2006.01) |
| A61K 8/97 | (2006.01) |
| A61Q 11/00 | (2006.01) |
| C07J 17/00 | (2006.01) |
| A23L 27/30 | (2016.01) |

(52) U.S. Cl.
CPC ............. *A23L 1/2363* (2013.01); *A23L 27/36* (2016.08); *A61K 8/63* (2013.01); *A61K 8/97* (2013.01); *A61Q 11/00* (2013.01); *C07J 17/005* (2013.01); *Y02P 20/544* (2015.11)

(58) Field of Classification Search
None
See application file for complete search history.

(56) References Cited

U.S. PATENT DOCUMENTS

2011/0027413 A1*  2/2011  Jia ........................ A23L 1/2366
                                                                  426/3

OTHER PUBLICATIONS

Drake del Castillo. Enumeration des Rubaicees trouvees au Tonkin par M. Malansa en 1885-89. Journal de Botanique 1895, pp. 213-220 (Title page and pp. 213 and 216 included). Machine translation of article from Latin and French included.*
MSDS for sodium methoxide downloaded Sep. 16, 2016 from http://www.sciencelab.com/msds.php?msdsId=9927332.*
The Evans Research Group. pKa's of acids and alcohols, downloaded Sep. 16, 2016 from http://evans.harvard.edu/pdf/evans_pka_table.pdf.*
USPTO 35 USC 101Examples of Nature Based Products, downloaded Sep. 16, 2016 from https://www.uspto.gov/patents/law/exam/mdc_examples_nature-based_products.pdf.*
Choi et al: "Abrusosides A-D, Four Novel Sweet-Tasting Triterpene Glycosides From the Leaves of Abrus Precatorius," Journal of Natural Products vol. 52, No. 5, pp. 1118-1127 (Sep.-Oct. 1989).
Suttisri et al: "Periandrin V, a Further Sweet Triterpene Glycoside From Periandra Dulcis," Phytochemistry, vol. 34, No. 2, pp. 405-408 (1993).
Hiura et al: "Taste-Modifying Triterpene Glycosides From Staurogyne Merguensis," Phytochemistry, vol. 43, No. 5, pp. 1023-1027 (1996).
Yoshikawa et al: "Characterization of New Sweet Triterpene Saponins from Albizia myriophylla," J. Nat. Prod., vol. 65, No. 11, pp. 1638-1642 (Nov. 11, 2002).
Suttisri et al: "Plant-derived triterpenoid sweetness inhibitors," Journal of Ethnopharmacology, vol. 47, No. 1, pp. 9-26 (1995).

* cited by examiner

*Primary Examiner* — Frederick Krass
*Assistant Examiner* — Michael P Cohen
(74) *Attorney, Agent, or Firm* — Dilworth & Barrese, LLP

(57) ABSTRACT

The invention relates to triterpenes and triterpene glycosides of the formula (I) and/or physiologically acceptable salts thereof, preferably naturally occurring triterpenes and triterpene glycosides from *Mycetia balansae* and/or physiologically acceptable salts thereof and orally consumable formulations comprising one or a plurality of these triterpenes and triterpene glycosides and/or physiologically acceptable salts thereof. The invention further relates to the use of these triterpenes and triterpene glycosides and/or physiologically acceptable salts thereof, preferably an extract of *Mycetia balansae*, for generating a sweet impression in an orally consumable formulation or for reinforcing the sweet impression of an orally consumable formulation comprising at least one further, preferably naturally occurring, sweet-tasting substance. Finally, the invention also relates to a method for producing an orally consumable formulation and a method for generating and/or reinforcing a sweet impression of an orally consumable formulation.

7 Claims, 3 Drawing Sheets

ORALLY CONSUMABLE FORMULATIONS COMPRISING CERTAIN SWEET-TASTING TRITERPENES AND TRITERPENE GLYCOSIDES

The invention relates to triterpenes and triterpene glycosides of the following formula (I) and/or physiologically acceptable salts thereof, preferably naturally occurring triterpenes and triterpene glycosides of *Mycetia balansae* and/or physiologically acceptable salts thereof and orally consumable formulations comprising one or a plurality of these triterpenes and triterpene glycosides and/or physiologically acceptable salts thereof. The invention further relates to the use of these triterpenes and triterpene glycosides and/or physiologically acceptable salts thereof, preferably an extract of *Mycetia balansae*, for generating a sweet impression in an orally consumable formulation or for reinforcing the sweet impression of an orally consumable formulation comprising at least one further, preferably naturally occurring, sweet-tasting substance. Finally, the invention also relates to a method for producing an orally consumable formulation and a method for generating and/or reinforcing a sweet impression of an orally consumable formulation.

Foods or stimulants that have a high sugar content (especially saccharose, lactose, glucose or fructose or mixtures thereof) are generally strongly preferred by consumers due to the sweetness. On the other hand, it is generally known that a high content of easily metabolisable carbohydrates causes a big increase in the blood sugar level, leads to the formation of fat deposits and ultimately can lead to health problems such as overweight, obesity, insulin resistance, adult-onset diabetes and late complications thereof. To make matters particularly worse, many of the above-mentioned carbohydrates can additionally impair dental health as they are broken down into, for example, lactic acid by certain types of bacteria in the oral cavity and can attack the tooth enamel of juvenile or adult teeth (caries).

It has therefore long been a goal to reduce as much as possible the sugar content of foods and/or stimulants, the preferred goal being to achieve this reduction with the smallest possible reduction in sweet impression. An appropriate measure consists in using sweeteners: they are chemically uniform substances that have no or only a very low calorific value themselves and simultaneously cause a strong sweet taste impression; the substances are generally not cariogenic (an overview can be found, for example, in the Journal of the American Dietetic Association 2004, 104 (2), 255-275). The so-called bulk sweeteners such as sorbitol, mannitol or other sugar alcohols are indeed to some extent excellent sweetening agents and can also partially replace the remaining alimentary properties of sugars but, with over-frequent intake, lead to osmotically-induced digestion problems in a proportion of the population. Through their low use concentration, the non-nutritive, highly-intensive sweeteners are well suited for introducing sweetness into food. However, a number of these sweeteners are not of natural origin (sucralose, cyclamate, acesulfame K, saccharin, aspartame), display taste problems through dissimilar time-intensity profiles compared to sugar (e.g. sucralose, steviol glycosides, cyclamate), a bitter and/or astringent aftertaste (e.g. acesulfame K, saccharin, steviol glycosides, rebaudiosides), and pronounced, additional flavouring impressions (e.g. glycerrhyzic acid ammonium salt). Some of the sweeteners are not particularly heat-stable (e.g. thaumatin, brazzein, monellin), are not stable in all applications (e.g. aspartame) and partly have a very long-lasting sweet effect (strong sweet aftertaste, e.g. saccharin, sucralose, steviol glycosides, rebaudiosides, neotame, advantame, superaspartame).

For this reason, it is desirable to find sweeteners that have or impart an intensive sweet taste similar to cane sugar, which preferably are also naturally occurring or easily obtainable from naturally occurring substances and moreover are preferably stable and/or widely usable in orally consumable formulations.

Another possibility for lowering the calorific content of foods or beverages—without using non-nutritive sweeteners—consists in reducing the sugar content of foods and/or stimulants and adding sensorially weak or imperceptible substances that directly or indirectly reinforce the sweetness such as described in WO 2005/041684. However, the substances described in WO 2005/041684 are explicitly of non-natural origin and, from a toxicology perspective, are thus more difficult to assess than substances of natural origin, particularly if the latter occur in foods or stimulants or originate from raw materials for obtaining foods or stimulants. Such substances of natural origin (pyridinium betaines) are described in EP 1 291 342; although it is not selectively the sweet taste but also other flavours such as umami or saltiness that are influenced by them. In addition, the purification of the disclosed substances requires considerable expenditure and/or they are difficult to produce synthetically.

The use of hesperetin is recommended in WO 2007/0148979 A1 and phloretin in WO 2007/107596 A1 as a reinforcer of the sweet taste of sugar-reduced alimentary or stimulant formulations. However, when using hesperetin and phloretin, the relatively weakly pronounced effect in foods and stimulants, the high proportions of proteins, particularly denatured proteins or polysaccharides such as yoghurt products, are occasionally disadvantageous. In addition, hesperetin has the disadvantage of not being sufficiently effective in very acidic or carbonated applications such as lemonades or cola drinks.

For this reason, it was desirable to find an option of being able to lower the content of sweet-tasting compounds in orally consumable formulations while retaining the same sweet impression so that sugar-reduced formulations are developed. In particular, there is a need for agents that reinforce a given sweet impression, also particularly over and above a purely additive effect.

Accordingly, the primary object of the present invention was to find substances (individual substances or substance mixtures), which can generate a sweet impression (i.e. have an intrinsic sweetness) and/or can reinforce the sweet impression of other sweet-tasting substances.

Furthermore, appropriate orally consumable formulations should be indicated in which the sweet impression is generated by these substances or whose sweet impression is reinforced by these substances at predominantly unchanged concentration of further sweet-tasting compounds or in which the content of further compounds generating a sweet taste impression is reduced while retaining the same sweet impression, whereby preferably there should be no or only to a negligible extent negative sensorial side effects.

In this arrangement, it would be advantageous if these substances occurred naturally or could be produced from natural and sustainable substances or raw materials. In particular, the substances imparting the sought-after sweet impression or reinforcing the sweet impression should preferably already be active at low concentrations. Furthermore, the sought-after substances should have the widest possible range of applications, i.e. able to be incorporated into many different orally applicable types of application and product and accordingly be combinable and compatible with many different orally consumable starting, auxiliary, carrier, additive and/or active substances.

This object is achieved according to the invention by the compounds of the formula (I) (called balansins in this text) or the physiologically acceptable salts of the compounds of the formula (I)

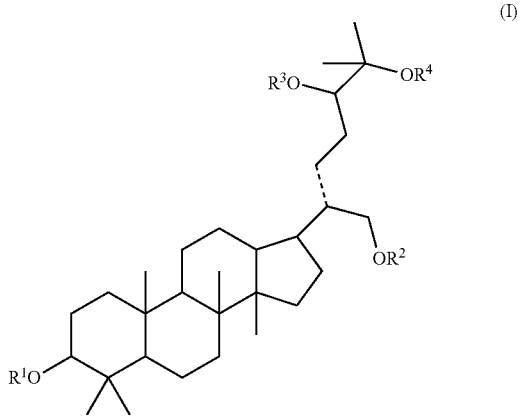

(I)

where
the dotted line represents a single or a double bond, and $R^1$, $R^2$, $R^3$ and $R^4$ each represent independently of each other hydrogen or a sugar residue, preferably a monosaccharide residue or an oligosaccharide residue,
characterised in that the countercation of the physiologically acceptable salt of the compound of the formula (I) is preferably selected from the group consisting of single positively charged cations from the first primary and secondary group, ammonium ion, trialkyl ammonium ions, divalently charged cations from the second secondary group, trivalent cations from the third primary and secondary group, and preferably selected from the group consisting of $Na^+$, $K^+$, $NH_4^+$, $Ca^{2+}$, $Mg^{2+}$, $Al^{3+}$ and $Zn^{2+}$.

BRIEF DESCRIPTION OF THE DRAWINGS

The present application will be described in greater detail with reference to the accompanying drawings, in which.

DETAILED DESCRIPTION OF THE INVENTION

Figure 1:
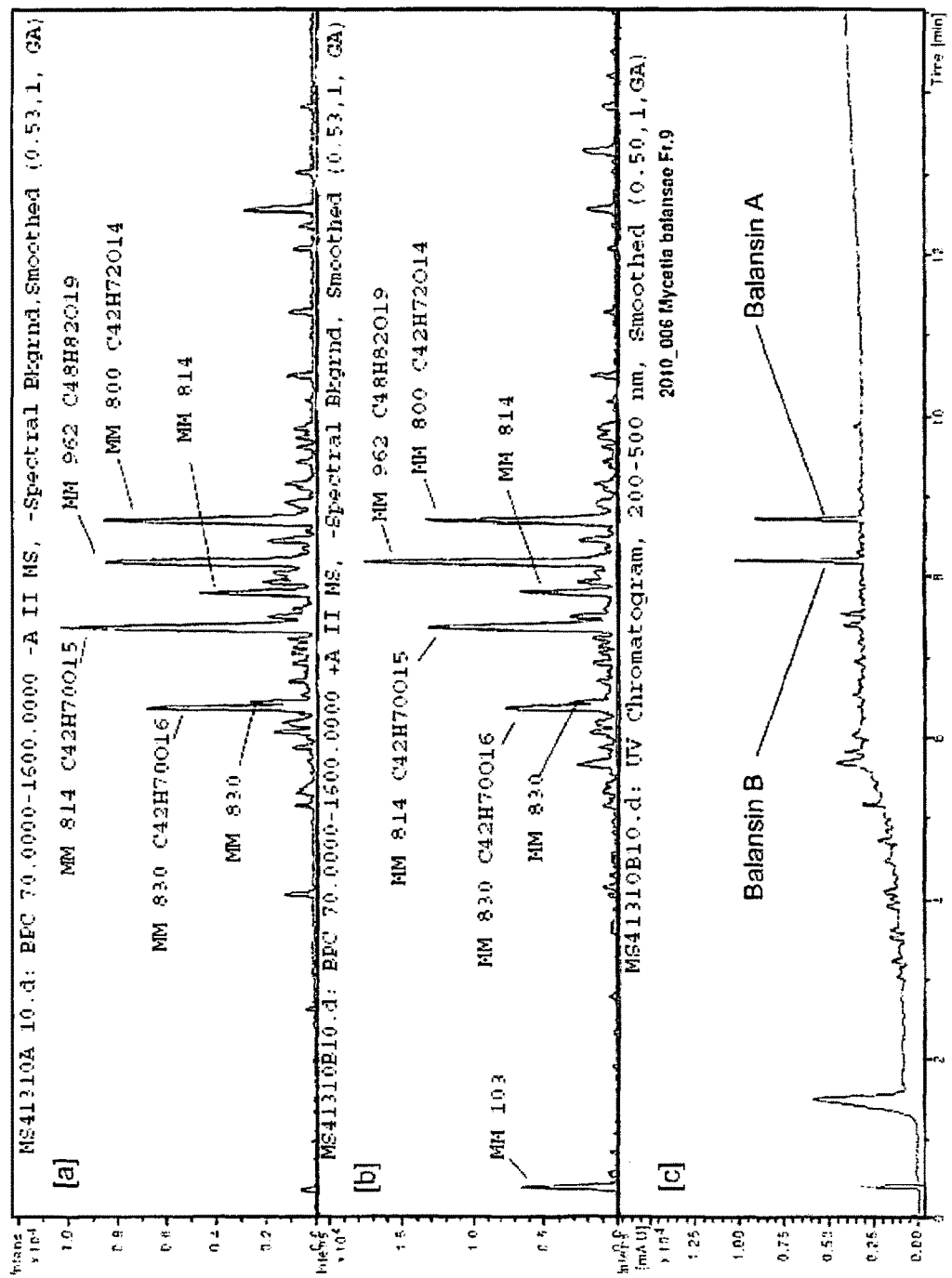
FIG. 1 is an LC-MS chromatogram of a plant extract according to the present invention.

The compounds according to the invention of the formula (I), as well as the preferred compounds according to the invention of the formula (II) and (III) described below, can be present in the form of their different possible stereoisomers and random mixtures of the different possible stereoisomers and can be used within the context of the present invention.

Provided a compound of the formula (I) comprises one or a plurality of sugar residues, said sugar residues can be α- or β-configured in each case independently of each other. This applies both to the bonding to the oxygen atom, via which the residues $R^1$, $R^2$, $R^3$ and $R^4$ are bonded to the triterpene skeleton and to the bonding of each of the simple sugar building blocks to each other, which form the respective sugar residue.

In the formula (I), one, two or three of the residues $R^1$, $R^2$, $R^3$ and $R^4$ preferably denote hydrogen and one, two or three of the residues $R^1$, $R^2$, $R^3$ and $R^4$ a sugar residue.

Preferred compounds of the formula (I) and/or physiologically acceptable salts of a compounds of the formula (I) are those in which at least one of the residues $R^1$, $R^2$, $R^3$ and $R^4$ denotes hydrogen, preferably at least two of the residues $R^1$, $R^2$, $R^3$ and $R^4$ denote hydrogen, and
at least one of the residues $R^1$, $R^2$, $R^3$ and $R^4$ denotes a sugar residue, the sugar residue being preferably selected or the sugar residues each independently of each other being preferably selected from the group consisting of
(i) the monosaccharide residues glucosyl, mannosyl, galactosyl, rhamnosyl, fucosyl, arabinosyl and ribosyl,
and
(ii) the oligosaccharide residues of 2 to 10 simple sugar building blocks, said simple sugar building blocks being preferably selected from the group consisting of glucose, mannose, galactose, rhamnose, fucose, arabinose and ribose.

In the formula (I), two or three of the residues $R^2$, $R^3$ and $R^4$ denote hydrogen and the residue $R^1$ and optionally one of the residues $R^2$, $R^3$ and $R^4$ denote a sugar residue, said sugar residue being preferably selected or the sugar residues each independently of each other being preferably selected from the group consisting of
(i) the monosaccharide residues glucopyranosyl, mannopyranosyl, galactopyranosyl, rhamnopyranosyl, fucopyranosyl, arabinosyl and ribosyl,
and
(ii) the oligosaccharide residues of 2 to 8 simple sugar building blocks, said simple sugar building blocks being preferably selected from the group consisting of glucopyranose, mannopyranose, galactopyranose, rhamnopyranose, fucopyranose, arabinose and ribose.

One, two or all of the residues $R^2$, $R^3$ and $R^4$ in formula (I) preferably denote hydrogen.

The dotted line in formula (I) preferably represents a double bond.

According to the invention, compounds of the formula (II) or a physiologically acceptable salt of a compound of the formula (II) are preferred.

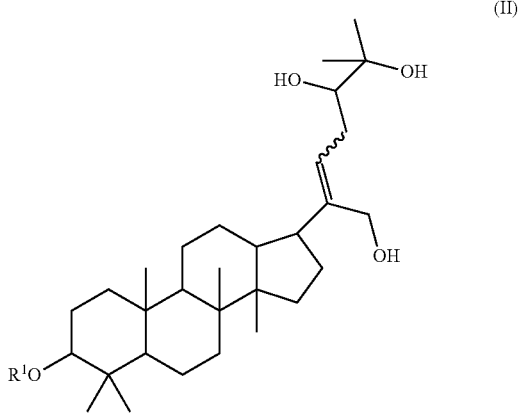

(II)

where

R¹ is a mono-, di-, tri-, tetra- or pentasaccharide residue, preferably selected from the group consisting of (i) glucosyl, mannosyl, galactosyl, rhamnosyl, fucosyl, arabinosyl and ribosyl, and (ii) the oligosaccharide residues of 2 to 5 simple sugar building blocks, said simple sugar building blocks being selected from the group consisting of glucose, mannose, galactose, rhamnose, fucose, arabinose and ribose.

In this arrangement, according to general drawing conventions, the zig-zag line in the formula (II) stands for an (E)- or a (Z)-configured double bond.

According to the invention, compounds of the formula (III) or a physiologically acceptable salt of a compound of the formula (III) are particularly preferred.

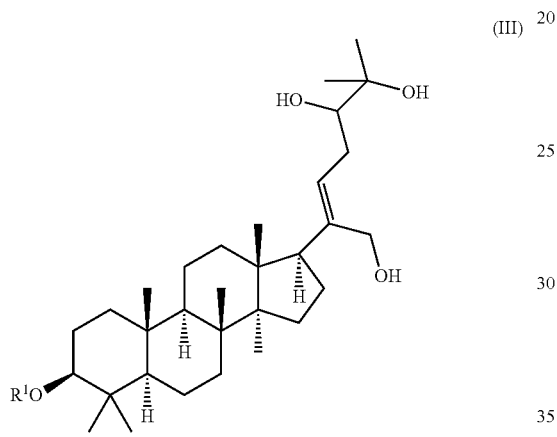

(III)

where

R¹ is a mono-, di-, tri-, tetra- or pentasaccharide residue, selected from the group consisting of (i) glucosyl, mannosyl, galactosyl, rhamnosyl, fucosyl, arabinosyl and ribosyl, and (ii) the oligosaccharide residues of 2 to 5 simple sugar building blocks, said simple sugar building blocks being selected from the group consisting of glucose, mannose, galactose, rhamnose, fucose, arabinose and ribose.

According to the invention, compounds of the above formula (III) or a physiologically acceptable salt of a compound of the above formula (III) are further preferred, where R¹ is a mono-, di-, tri-, tetra- or pentasaccharide residue, selected from the group consisting of (i) glucopyranosyl, galactopyranosyl and rhamnopyranosyl, and (ii) the oligosaccharide residues of 2 to 4 simple sugar building blocks, said simple sugar building blocks being selected from the group consisting of glucopyranose, galactopyranose and rhamnopyranose, the simple sugar building blocks for their part being preferably bonded to each other at positions 2, 4 and/or 6.

According to the invention, the two following compounds and/or stereoisomers thereof or a physiologically acceptable salt of these compounds (hereinafter called A and B, respectively) are most particularly preferred.

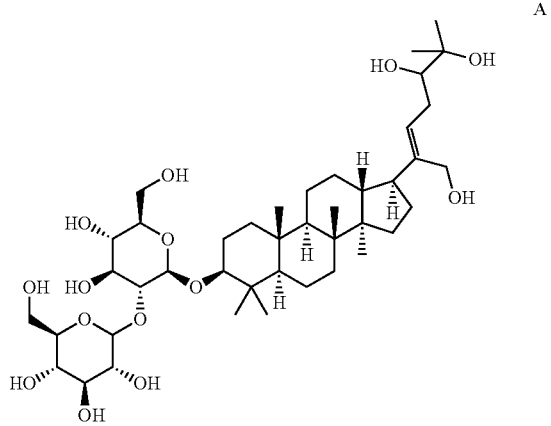

A

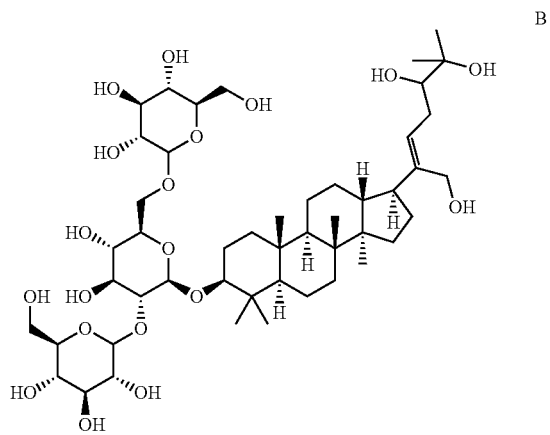

B

According to the invention, the two following stereoisomers of the compounds A and B (hereinafter called Balansin A and Balansin B) are most particularly preferred.

Balansin A

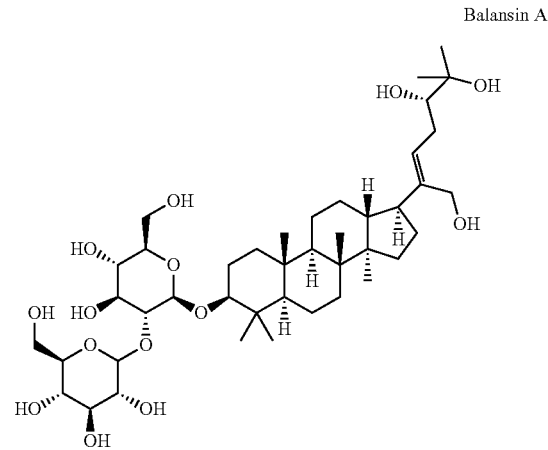

-continued

Balansin B

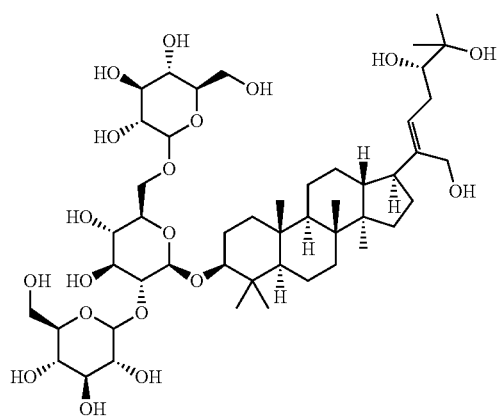

According to the invention, mixtures of two, three or more different compounds of the formulae (I), (II) or (III) can also be used, such a mixture preferably comprising two, three or more of the compounds identified above as preferable.

The compounds according to the invention of the formula (I), (II) and/or (III) can also be preferably present as mono- or, for example in the case of several hydroxy groups, polyvalent anions, the single positively charged cations of the first primary and secondary group, the ammonium ion, a trialkyl ammonium ion, the divalently charged cations of the second secondary group, and the trivalent cations of the 3rd primary and secondary group preferably serving as countercation, preferably $Na^+$, $K^+$, $NH_4^+$, $Ca^{2+}$, $Mg^{2+}$, $Al^{3+}$ and $Zn^{2+}$.

If preferred and/or particularly preferred compounds of the formulae (I), (II) and/or (III) are cited within the present text, the salts of such compounds according to the invention are obviously also preferred and/or particularly preferred.

Thus, one, two or a plurality of different salts of one, two or a plurality of different compounds of the formula (I), (II) and/or (III) as defined above Or a mixture of one, two or a plurality of different compounds of the formula (I), (II) and/or (III) as defined above and one, two or a plurality of different salts of one, two or a plurality of different compounds of the formula (I), (II) and/or (III) as defined above are preferred according to the invention, characterised in that the countercation of the/countercations of one, a plurality of or all the salts is/are preferably selected from the group consisting of $Na^+$, $K^+$, $NH_4^+$, $Ca^{2+}$, $Mg^{2+}$, $Al^{3+}$ and $Zn^{2+}$.

Accordingly, the present invention also relates to a mixture comprising or consisting of two, three or a plurality of compounds as defined above, preferably in one of the embodiments identified as preferred, or one, two or a plurality of different compounds as defined above and one, two or a plurality of different physiologically acceptable salts of one, two or a plurality of different compounds as defined above, preferably in one of the embodiments identified as preferred, or two, three or a plurality of physiologically acceptable salts of the compounds as defined above, preferably in one of the embodiments identified as preferred, whereby, provided one or a plurality of physiologically acceptable salts of one or a plurality of compounds as defined above is or are available in the mixture, preferably the countercations of all physiologically acceptable salts of the compounds as defined above are selected from the group consisting of $Na^+$, $K^+$, $NH_4^+$, $Ca^{2+}$, $Mg^{2+}$, $Al^{3+}$ and $Zn^{2+}$.

Particularly preferred mixtures according to the invention comprise Balansin A and/or Balansin B, preferably Balansin A and Balansin B, preferably Balansin A and Balansin B and optionally one, two, three or more further compounds of the formulae (I), (II) and/or (III) and/or optionally one, two, three or a plurality of physiologically acceptable salts of one or a plurality of compounds of the formulae (I), (II) and/or (III).

Particularly preferred mixtures according to the invention comprise a physiologically acceptable salt of Balansin A and/or of Balansin B, preferably a $Na^+$, $K^+$, $NH_4^+$, $Ca^{2+}$, $Mg^{2+}$, $Al^{3+}$ or $Zn^{2+}$ salt of Balansin A and of Balansin B and optionally one, two, three or a plurality of further physiologically acceptable salts of one or a plurality of compounds of the formulae (I), (II) and/or (III).

The compounds of the formulae (I), (II) and (III) can be obtained from the plant *Mycetia balansae* Drake and be enriched or isolated, for example, from the extracts of *Mycetia balansae*, or can be produced by derivatisation or conversion of the triterpenes and/or triterpene glycosides occurring in this plant or available in the extracts, for example, by hydration, glycosidation, glycolysis, salt formation and similar methods known to the person skilled in the art.

In particular, the glycoside pattern can be changed, for example, by glycosidation or transglycosidation or, more precisely, transferglycosidation with the aid of appropriate enzymes, e.g. by using glycosidases or transglycosidases as enzymes, or also organisms are used such as, e.g., bacteria with appropriate activities (e.g. according to KR 888694). In this arrangement, other glycosides or glycans that are not preferred according to the invention can be used as reactants, but preferred glycosides or glycans are those formulated from glucose, mannose, galactose, rhamnose, fucose, arabinose and ribose.

The compounds of the formula (I) where the dotted line represents a single bond can be produced from the corresponding compounds of the formula (I) where the dotted line represents a double bond, by homogeneous or heterogeneous metal-catalysed hydration or transferhydration known to the person skilled in the art or also by hydrogenation accomplished by enzyme or organisms.

*Mycetia balansae* Drake (family Rubiaceae, genus: *Mycetia*; Global Biodiversity Information Facility: confirmed by Kew Garden record number Kew-130690, http://data.gbif.org/species/14242490/) is a plant which is common in Southeast Asia.

There is no description in the literature of *Mycetia balansae* Drake being consumed. There was only oral anecdotal evidence, if any, of the local population chewing the fresh, i.e. not dried, leaves. This did not include reports of it being used to sweeten orally consumable formulations such as foods or stimulants. Likewise, the chemical composition either of the species *Mycetia balansae* Drake or of other *Mycetia* genera has not been described. Therefore, the balansins of the formula (I) are novel. The compounds of the formula (I) and salts thereof have up till now neither been described as an ingredient of *Mycetia balansae* nor been known from other natural or synthetic sources.

It was thus surprising and could not be predicted by the person skilled in the art that the above-described balansins according to the invention of the formula (I) can cause a strong sweet impression or reinforce to a significant and pronounced degree the sweet impression of other sweet-tasting substances such as, e.g., an aqueous saccharose solution.

Compared to plant parts, particularly the (preferably fresh) leaves of *Mycetia balansae*, the compounds according to the invention of the formula (I), (II) and/or (III) and/or salts thereof and/or a mixture according to the invention (as defined above) are according to the invention preferably used in enriched form, preferably in purified or isolated form.

The fresh or dried plant *Mycetia balansae* as such is not an object of the present invention. A fresh or dried plant part (for example, leaves) of *Mycetia balansae* as such is also not an object of the present invention, in this case particularly not the fresh or dried leaves of *Mycetia balansae*.

The mixture resulting from chewing, particularly from chewing by a person, the fresh leaves of *Mycetia balansae* is preferably also not an object of the present invention. A saliva extract, preferably not a human saliva extract, resulting from chewing the fresh leaves of *Mycetia balansae* is preferably also not an object of the present invention. In a preferred embodiment, an orally consumable formulation according to the invention is free of human saliva, preferably free of saliva.

According to the invention, the plant or plant parts of *Mycetia balansae* can also be used in dried and ground, preferably powder, form.

An orally consumable formulation according to the invention, for example in the form of a semi-finished product, can for example comprise the plant or plant parts of *Mycetia balansae*, preferably in dried and powder form, and one or a plurality of additive, carrier and/or auxiliary substances suitable for consumption. A semi-finished product according to the invention preferably comprises one or a plurality of the compounds of the formula (I) and/or one or a plurality of physiologically acceptable salts of the compounds of the formula (I) and one or a plurality of additive, carrier and/or auxiliary substances suitable for consumption which are stable at 20° C. and 1013 mbar.

The invention also relates to a plant extract, preferably a plant extract of *Mycetia balansae*, comprising one or a plurality of compounds of the formula (I) or a physiologically acceptable salt of a compound of the formula (I), or a mixture according to the invention, the total amount of these compounds and of the physiologically acceptable salts of these compounds preferably being in the range of 0.00001 to 99 wt %, preferably in the range of 0.0001 to 95 wt %, particularly preferably in the range of 0.0005 to 80 wt %, most particularly preferably in the range of 0.001 to 30 wt %, based on the dry mass of the extract.

The term "dry mass" in the broader sense is understood to mean the mass of an extract according to the invention free of water and extractant. Such a mass can be obtained, for example, by completely removing the extractant through distillation or other evaporative methods (including the water which may originate from the plant material) after completion of the extraction step or steps of an extraction method according to the invention (see below).

The term "dry mass" in the narrower sense is understood to mean the total mass of all solids of the extract based on 20° C. at 1013 mbar.

Within the context of the present text, the "solid" state and the term "solid substance" refer to 20° C. at 1013 mbar.

Extractants suitable for the foods and stimulants sector are, for example, water, ethanol, methanol, 1-propanol, 2-propanol, 1,2-propandiol, glycerine, acetone, dichloromethane, acetic acid ethyl ester (ethyl acetate), diethyl ether, hexane, heptane, triacetin, vegetable oils or fats, supercritical carbon dioxide and mixtures thereof. Particularly preferred in this arrangement are water, ethanol, methanol, 1-propanol, 2-propanol, glycerine, 1,2-propandiol or mixtures of the aforesaid non-aqueous extractants with water.

A preferred plant extract according to the invention is obtainable or obtained by a method with the following step:
a) single or multiple extraction of plant material from *Mycetia balansae* with a, preferably liquid, extractant selected from the group consisting of water, ethanol, methanol, 1-propanol, 2-propanol, glycerine, 1,2-propandiol, supercritical carbon dioxide, acetic acid ethyl ester and mixtures thereof, and, if necessary, one or a plurality of further steps as follows:
b) if necessary, concentration of the primary extract obtained in Step a), preferably by one or a plurality of evaporative or pervaporative methods,
c) if necessary, treatment of the primary extract (concentrated, if necessary, in Step b)) with or on adsorbents, preferably selected from the group consisting of silica gel, modified silica gel, activated carbon, zeolith, bentonite, diatomaceous earth, aluminium oxide, basic or acidic or neutral, optionally macroporous, ion exchanger, preferably in batch or column method, if necessary with the aid of further extractants, a purified extract (secondary extract) being obtained,
d) if necessary, drying the secondary extract obtained in Step c), preferably by an evaporative or pervaporative method,
e) if necessary, mixing the dried secondary extract obtained in Step d) with a suitable diluent or with a mixture of two or a plurality of diluents, preferably selected from the group consisting of ethanol, isopropanol, 1,2-propylene glycol, vegetable oil triglycerides, diacetin, triacetin and glycerine, a solution being preferably obtained.

An extract according to the invention of *Mycetia balansae*, which is preferably used for the production of an orally consumable formulation according to the invention, can be obtained preferably from the fresh and/or dried plant or parts thereof (for example, roots, stalks, rind, pith, leaves, flowers and/or fruits), preferably from the dried, above-ground plant parts (here, preferably leaves, stalks, flowers and/or fruits) of *Mycetia balansae* by means of extraction.

The plant or plant parts of *Mycetia balansae* can also be used in dried and ground, preferably powder, form for the production of an extract according to the invention.

A plant extract according to the invention, preferably of *Mycetia balansae*, is preferably obtained by an extraction method according to the invention, preferably from *Mycetia balansae*.

In a preferred embodiment, a plant extract according to the invention comprises besides one or a plurality of compounds of the formula (I) additionally only such compounds that are solid at 20° C. and 1013 mbar and which are preferably not free carbohydrates, particularly not sweet-tasting free carbohydrates.

The plant extract according to the invention preferably includes only such compounds in terms of the aforesaid that can be extracted from *Mycetia balansae* by means of ethyl acetate, ethanol or methanol and by means of a methanol-ethanol, methanol-water, methanol-ethanol-water or ethanol-water mixture, or supercritical carbon dioxide (if necessary, in combination with a polarity-increasing agent such as ethanol).

The extraction period of the extraction step(s) is preferably 5 minutes to 24 h in each case, preferably 15 minutes to 18 h in each case.

Step a) is preferably carried out by extraction through stirring, Soxhlet extraction, high-pressure extraction, microwave-accelerated extraction, ultrasound-accelerated extraction, counterflow extraction, percolation or in a sieve basket method.

One, a plurality of or all extractions (extraction steps) of a method according to the invention are preferably carried out in each case at temperatures in the range of −80° C. up to the corresponding boiling point of the extractant or extractant mixture, preferably in the range of 0 to 200° C., if necessary at a pressure in the range of 1 bar to 1000 bar. Each extraction step is carried out preferably for the period of 5 minutes to 24 h, preferably by stirring (preferably simple stirring), high-pressure extraction, microwave-accelerated extraction, ultrasound-accelerated extraction, percolation or counterflow extraction.

In this arrangement, evaporative or pervaporative methods can be, for example, distillation, sublimation, steam distillation, freeze-drying, pervaporative membrane method or spray drying, whereby suitable auxiliary and/or carrier substances can also be added thereto before and/or during this method.

The extraction step(s) can be carried out preferably by stirring (e.g. simple stirring), high-pressure extraction, microwave-accelerated extraction, ultrasound-accelerated extraction, percolation and/or counterflow extraction.

A plant extract according to the invention of *Mycetia balansae* is obtained preferably from fresh and/or dried above-ground plant parts, preferably leaves, stalks, flowers and/or fruits, preferably in dried and comminuted form, preferably comprising the following step:

a) extraction of plant material from *Mycetia balansae* with a liquid extractant selected from the group consisting of water, ethanol, methanol, 1-propanol, 2-propanol, glycerine, 1,2-propandiol, acetic acid ethyl ester and mixtures thereof, preferably at a temperature in the range of 0° C. up to the boiling point of the extractant or extractant mixture used, optionally at a pressure in the range of 1 bar to 1000 bar.

The extractant(s) or extractant mixtures can be used in each case preferably individually or in binary or ternary mixtures or also consecutively in an increasing or decreasing polarity sequence.

An extraction method according to the invention for the production of a plant extract according to the invention preferably comprises an extraction step with a less polar, preferably non-polar extractant, which is carried out before Step a). In this way, in such a pretreatment step preceding Step a), undesirable companion substances such as fats and waxes are first extracted from the plant material and separated so that a plant extract obtained in this way according to the invention is easier to further process.

In addition, our own studies have surprisingly shown that a multiplicity of companion substances and by-products with objectionable taste notes such as noticeably bitter notes do not or no longer exist in an extract present according to Step a) in accordance with this procedure of consecutive extraction. In a preferred embodiment, all substances with objectionable taste notes are removed or prevented in this way.

Before extraction according to Step a), the plant material can be subjected to an extraction by a less polar agent. Particularly preferred for such a pretreatment of the plant material are the less polar extractants such as, e.g., butane, propane, isobutane, tert-butyl methyl ether, dichloromethane, n-heptane, n-hexane or mixtures thereof, the extraction preferably being carried out at a temperature in the range of −80° C. to the corresponding boiling point of the extractant or extractant mixture at the pressure used during the extraction step(s). The pressure during the extraction step(s) for the pretreatment of the plant material is preferably in the range of 0.1 to 1000 bar, preferably in the range of 0.5 to 250 bar.

The extraction for pretreatment of the plant material is carried out before carrying out the extraction(s) according to Step a) preferably at a temperature in the range of −80° C. to 200° C.

If the critical point of the extractant or extractant mixture is reached, the maximum temperature can also be selected up to 200° C. such as, e.g., in extraction with supercritical carbon dioxide, propane, butane or isobutane, if necessary, with the addition of further extractants and/or solvents. The extraction particularly with aqueous mixtures can also be carried out in the presence of pH-regulating acids, bases or buffer mixtures.

A consecutive extraction method with two, three, four or a plurality of consecutively carried-out extractions is preferred, the extractants used preferably becoming increasingly polar with each subsequent extraction. Here, it is preferable to start with a non-polar extractant and to subject the plant parts to be extracted to an extraction with a non-polar extractant. The non-polar extractant is removed after the first extraction has finished and a primary extract obtained from this extraction step. Next, the extraction of the plant parts already subjected to the first extraction step is repeated at least in a further step, an extractant of higher polarity being used and a corresponding primary extract being obtained from this extraction stage.

In this arrangement, the consecutive extraction can comprise a plurality of extraction steps, the last extraction step being preferably an extraction with water, ethanol, methanol, 1-propanol, 2-propanol, glycerine, 1,2-propandiol or a mixture of the aforesaid non-aqueous extractants with water. In this arrangement, it is preferred if the extract according to the invention used in the orally consumable formulations according to the invention has been obtained from a primary extract of the last extraction step.

The extract present according to Step a) and/or obtainable after Step b) can be optionally still further digested, for example, through enzymatic treatment (e.g. with cellulases for the digestion of cells), through treatment with acid (e.g. under pressure), through treatment with suitable basic solutions, e.g., of hydroxides, carbonates or hydrogen carbonates of sodium, potassium, calcium, magnesium and zinc, with acid ion exchangers or with steam, preferably at pressures in the range of 0.01 mbar to 100 bar, preferably in the range of 1 mbar to 20 bar.

The extract from Step a) can be optionally concentrated in a Step b) if necessary by distillation or other evaporative or pervaporative methods, if necessary until only solids or hardly volatile or non-volatile liquids are present.

The concentrated or, more precisely, dry primary extract of *Mycetia balansae* after Step b) contains preferably 0.001 to 80 wt %, preferably 0.005 to 50 wt %, particularly preferably 0.01 to 25 wt %, of balansins of the formula (I), in each case based on the dry mass of the concentrated primary extract.

Optionally, the, if necessary, concentrated primary extract can be purified in a Step c) by treatment with or on adsorbents (silica gel, modified silica gels (e.g. RP phases), activated carbon, zeoliths, bentonite, diatomaceous earth, aluminium oxide, basic or acidic or neutral [macroporous] ion exchangers), in batch or column method, if necessary also with the aid of further extractants, preferably one or a plurality of extractants selected from the group consisting of water, n-hexane, dichloromethane, formic acid, methanol, ethanol and 1,2-propylene glycol, a secondary extract being obtained.

The resulting secondary extract of *Mycetia balansae* according to Step c) can also be replaced by a proportion of 1-99 wt %, based on the dried secondary extract, of auxiliary and carrier substances suitable for consumption (e.g. maltodextrin, starch, natural or synthetic polysaccharides and/or vegetable gums such as modified starches or gum arabic) in order to optimise the production of a dried secondary extract according to Step d).

Preferred auxiliary or carrier substances in Step d) are maltodextrin, starch, natural or synthetic polysaccharides and/or vegetable gums such as modified starches or gum arabic, whereby, if necessary, additionally one or more further substances suitable for consumption can be used, preferably selected from the group consisting of:
(i) diluents such as ethanol, 1,2-propylene glycol, glycerine, diacetin, triacetin and/or vegetable oil triglycerides,
(ii) colouring agents, e.g. approved food colourings and colouring plant extracts,
(iii) stabilisers, preservatives, antioxidants and viscosity-controlling substances.

The concentrated and/or dried secondary extract of *Mycetia balansae* after Step d) preferably contains a total amount of compounds of the formula (I) in the range of 0.001 to 99 wt %, preferably in the range of 1 to 99 wt %, further preferably in the range of 5 to 95 wt %, particularly preferably 10 to 90 wt %, in each case based on the dried mass of the concentrated secondary extract.

The plant extracts according to the invention are, preferably in Step e), preferably mixed with a diluent or diluent mixture, preferably selected from the group consisting of water, propylene glycol, glycerine and ethanol and mixtures thereof, and a solution produced, whereby the complete dissolving of the compounds of balansins can be facilitated or accelerated by mild heating.

The total amount of plant extract according to the invention in such a solution is preferably in the range of 1-20 wt %, preferably in the range of 2-10 wt %, particularly preferably in the range of 4-6 wt %.

Such a solution is preferably produced with a diluent mixture of the aforesaid diluents, preferably selected from the group consisting of water-propylene glycol, water-glycerine, water-ethanol, glycerine-ethanol, glycerine-propylene glycol and propylene glycol-ethanol.

The diluent or diluent mixtures used in Step e) of an extraction method according to the invention are preferably suitable for consumption as, in such a case, the extracts according to the invention present according to Step e), particularly the extracts present as solution, are particularly suitable for direct use in orally consumable formulations, preferred orally consumable formulations being selected from the group consisting of alimentary formulations, dietary supplement formulations, stimulant formulations, oral pharmaceutical formulations, mouth care products (oral hygiene products) and flavouring compositions.

The invention further relates to an orally consumable formulation, comprising a sensorily active amount of a compound according to the invention as defined above and/or a physiologically acceptable salt according to the invention of a compound as defined above, a mixture according to the invention as defined above, and/or an extract according to the invention as defined above, the orally consumable formulation being preferably selected from the group consisting of alimentary formulations, dietary supplement formulations, stimulant formulations, oral pharmaceutical formulations, mouth care products, flavouring compositions and cosmetic formulations.

To determine the sweet impression of the extracts according to the invention or of the compounds according to the invention of the formula (I) compared to an aqueous saccharose solution, an aqueous solution of one or a plurality of compounds of the formula (I) is produced in the same concentration as is present in the orally consumable formulation under study. This aqueous solution is then compared and rated for taste by a group of at least five persons against a reference series of different saccharose concentrations in water. In this way, the saccharose equivalence is determined (indicated in saccharose equivalents), in other words, the concentration of the saccharose solution, whose sweet impression is equivalent to the sweet impression of the concentration of compounds of the formula (I).

Preferred concentrations of the saccharose reference solution are 0; 0.25; 0.5; 0.75; 1; 1.5; 2; 3; 4 and 5 wt % saccharose in water. If necessary, other concentrations, particularly higher concentrations, can also be used for the reference series. The ascertained saccharose equivalent is obtained from the mean value of the individual rating of the individual panelists. The panelists are preferably persons who have experience in the field of tasting, are of different age and gender and come from different backgrounds.

Surprisingly, it was found that the compounds according to the invention of the formula (I) and/or the extracts according to the invention, preferably the extracts according to the invention of *Mycetia balansae*, can considerably reinforce even at very low concentrations the sweet taste and the sweet taste quality of sweet-tasting substances in orally consumable formulations according to the invention (preferably alimentary, mouth care or stimulant or cosmetic formulations for application in the region of the head).

The sweet-reinforcing effect of an extract according to the invention, preferably of an extract according to the invention of *Mycetia balansae*, is observed even in an amount of extract according to the invention of less than or equal to 1 wt % (i.e. 1 wt %), preferably 0.5 wt %, particularly preferably 0.1 wt %, in each case based on the total weight of an orally consumable formulation according to the invention.

The sweet-reinforcing effect of the compounds according to the invention of the formula (I), preferably as an ingredient of the extract according to the invention, preferably of an extract according to the invention of *Mycetia balansae*, is observed even in a total amount of compounds according to the invention of the formula (I) of less than 0.01 wt % (equivalent to 100 ppm) (ppm=parts per million), preferably less than 0.0050 wt % (equivalent to 50 ppm), in each case based on the total weight of an orally consumable formulation according to the invention.

As already explained above, mixtures according to the invention, plant extracts according to the invention and orally consumable formulations according to the invention are preferred that contain one or a plurality of the above-mentioned compounds identified as preferred and/or particularly preferred of the formulae (I), (II) and/or (III) or salts thereof. Particularly preferred are mixtures according to the invention, plant extracts according to the invention and orally consumable preparations according to the invention that contain Balansin A and/or Balansin B.

The present invention also relates to a method for (a) imparting a sweet taste impression and/or reinforcing a sweet taste impression of one, two or a plurality of sweet-tasting substances and/or (b) producing an orally consumable formulation according to the invention, preferably in one of the embodiments identified as preferred, with the following steps:
a) providing a compound according to the invention, preferably in one of the embodiments identified as preferred, and/or a physiologically acceptable salt of a compound according to the invention, preferably in one of the embodiments identified as preferred, a mixture according to the invention, preferably in one of the embodiments identified as preferred, and/or an extract according to the invention, preferably in one of the embodiments identified as preferred,
b) providing an orally consumable formulation, preferably comprising one, two or a plurality of further sweet-tasting substances,
c) bringing into contact or mixing of the ingredients provided in Step a) and b).

A method preferred according to the invention comprises the steps
a-i) producing an extract according to the invention, preferably in one of the embodiments identified as preferred, comprising a compound according to the invention, preferably in one of the embodiments identified as preferred, and/or a physiologically acceptable salt of a compound according to the invention, preferably in one of the embodiments identified as preferred, or a mixture according to the invention, preferably in one of the embodiments identified as preferred,
through extracting plant material, preferably plant material from *Mycetia balansae*;
a-ii) optional further processing of the extract produced in Step (a-i) into a further-processed product comprising a compound according to the invention, of a physiologically acceptable salt of a compound according to the invention, or of a mixture according to the invention,
b) providing an orally consumable formulation, preferably comprising one, two or a plurality of further sweet-tasting substances,
c) bringing into contact or mixing of the orally consumable formulation from Step b), which preferably comprises one, two or a plurality of further sweet-tasting substances, with the extract produced in Step a-i) and/or the further-processed product produced in Step a-ii).

Preferred are formulations to be orally consumed according to the invention, comprising one or a plurality of the compounds of the formula (I), (II) or (III) and/or one or a plurality of physiologically acceptable salts of a compound according to the invention of the formula (I), (II) or (III), in a total amount that is sufficient to generate a sweet perception in the formulations to be orally consumed, said perception being at least equal to that of a reference formulation which consists of a 2 wt % solution of saccharose in water.

A further aspect of the invention relates to formulations to be orally consumed (orally consumable formulations) containing one or a plurality of the compounds of the formula (I) and/or physiologically acceptable salts thereof and/or mixtures thereof in combination with at least a further sweet-tasting substance.

Preferred are formulations to be orally consumed according to the invention, comprising one or a plurality of the compounds of the formula (I), (II) or (III) and/or one or a plurality of physiologically acceptable salts of a compound according to the invention of the formula (I), (II) or (III), and at least a further sweet-tasting substance, which is present in a concentration that is sufficient to generate a sweet perception in the formulations to be orally consumed, said perception being at least equal to that of a reference formulation, which consists of a 2 wt % solution of saccharose in water.

In this arrangement, the sweet impression is preferably synergistically reinforced.

The object of the present invention is also a method to reinforce the sweet impression arising from tasting an orally consumable formulation, comprising the steps:
a) providing an orally consumable formulation, comprising one or a plurality of further sweet-tasting substances that together impart a sweet impression which is equal to or stronger than that of an aqueous saccharose solution with a concentration of 2 wt % saccharose,
b) providing
one of a plurality of compounds according to the invention of the formula (I),
or
an extract according to the invention, preferably of *Mycetia balansae*, comprising one or a plurality of compounds of the formula (I), here preferably 0.00001 to 99 wt %, preferably 0.0001 to 95 wt %, particularly preferably 0.0005 to 80 wt %, most particularly preferably 0.001 to 30 wt %, based on the dry mass of the extract,
c) mixing of the ingredients provided in Step a) and b).

Further sweet-tasting substances within the meaning of the invention can be naturally occurring, sweet-tasting substances of plant extracts but also synthetic sweet-tasting substances.

Naturally occurring sweet-tasting substances (including plant extracts) can be, for example, sweet-tasting carbohydrates (e.g. saccharose, trehalose, lactose, maltose, melizitose, melibiose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde, maltodextrins), sugar alcohols (e.g. erythritol, threitol, arabitol, ribitol, xylitol, sorbitol, mannitol, maltitol, isomalt, dulcitol, lactitol), proteins (e.g. miraculin, pentaidin, monellin, thaumatin, curculin, brazzein, mabinlin), D-amino acids (e.g. D-phenylalanine, D-tryptophan) or extracts or fractions obtained from natural sources containing these amino acids and/or proteins, neohesperidin dihydrochalcone, naringin dihydrochalcone, steviol glycosides, steviosides, steviolbioside, rebaudiosides, rebaudioside A, rebaudioside B, rebaudioside C, rebaudioside D, rebaudioside E, rebaudioside F, rebaudioside G, rebaudioside H, dulcosides, rubusoside, suavioside A, suavioside B, suavioside G, suavioside H, suavioside I, suavioside J, baiyunoside 1 baiyunoside 2, phlomisoside 1, phlomisoside 2, phlomisoside 3, and phlomisoside 4, abrusoside A, abrusoside B, abrusoside C, abrusoside D, cyclocaryoside A and cyclocaryoside I, osladin, polypodoside A, strogin 1, strogin 2, strogin 4, selligueain A, dihydroquercetin-3-acetate, perillartine, telosmoside $A_{15}$, periandrin I-V, pterocaryosides, cyclocaryosides, mukuroziosides, trans-anethole, trans-cinnamaldehyde, bryosides, bryonosides, bryonodulcosides, carnosiflosides, scandenosides, gypenosides, trilobatin, phloridzin, dihydroflavanols, hematoxylin, cyanine, chlorogenic acid, albiziasaponin, telosmosides, gaudichaudioside, mogrosides, mogroside V, hernandulcins, monatin, glycyrrhetinic acid and derivatives thereof, particularly glycyrrhizin (preferably as ammonium salt), and phyllodulcin, whereby, in the case of naturally occurring sweeteners, extracts or enriched fractions of these extracts can also be used, e.g. thaumatococcus extracts (katemfe bush), extracts of *Stevia* ssp. (particularly *Stevia rebaudiana*), Swingle extract (*Momordica* or *Siratia grosvenorii*, Luo-Han-Guo), extracts of *Glycerrhyzia* ssp. (particularly *Glycerrhyzia glabra*), *Rubus* ssp. (particularly *Rubus suavissimus*), citrus extracts, extracts of *Lippia dulcis*.

Preferred according to the invention is an orally consumable formulation, additionally comprising one, two, three, four, five, six, seven, eight, nine, ten or a plurality of further substances, selected from the following groups (a1) to (a5):

(a1) flavourings, preferably one, two, three, four, five or a plurality of flavourings being selected from the group consisting of: vanillin, ethyl vanillin, 2-hydroxy-4-methoxybenzaldehyde, ethyl vanillin isobutyrate (=3 ethoxy-4-isobutyryloxybenzaldehyde), Furaneol® (2,5-dimethyl-4-hydroxy-3(2H)-furanone) and derivatives (e.g. homofuraneol, 2-ethyl-4-hydroxy-5-methyl-3(2H)-furanone), homofuronol (2-ethyl-5-methyl-4-hydroxy-3(2H)-furanone and 5-ethyl-2-methyl-4-hydroxy-3(2H)-furanone), maltol and its derivatives (e.g. ethyl maltol), coumarin and its derivatives, gamma-lactones (e.g. gamma-undecalactone, gamma-nonalactone), delta-lactones (e.g. 4-methyl delta-lactone, massoia lactone, delta-decalactone, tuberolactone), methyl sorbate, divanillin, 4-hydroxy-2(or 5)-ethyl-5(or 2)-methyl-3(2H)furanone, 2-hydroxy-3-methyl-2-cyclopentenone, 3-hydroxy-4,5-dimethyl-2(5H)-furanone, fruit esters and fruit lactones (e.g. acetic acid n-butyl ester, acetic acid isoamyl ester, propionic acid ethyl ester, butyric acid ethyl ester, butyric acid n-butyl ester, butyric acid isoamyl ester, 3-methyl-butyric acid ethyl ester, n-hexanoic acid ethyl ester, n-hexanoic acid allyl ester, n-hexanoic acid n-butyl ester, n-octanoic acid ethyl ester, ethyl-3-methyl-3-phenylglycidate, ethyl-2-trans-4-cis-decadienoate), 4-(p-hydroxyphenyl)-2-butanone, 1,1-dimethoxy-2,2,5-trimethyl-4-hexane, 2,6-dimethyl-5-hepten-1-al and phenylacetaldehyde;

(a2) carbohydrates selected from the group consisting of saccharose, trehalose, lactose, maltose, melizitose, melibiose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde, maltodextrins and plant formulations containing one or a plurality of the cited carbohydrates, preferably in a proportion of at least 5 wt %, preferably at least 15 wt %, whereby the carbohydrates can also be present as a naturally occurring or synthetically produced mixture, in this arrangement particularly as honey, invert sugar syrup or highly enriched fructose syrup from maize starch, and the physiologically acceptable salts of these carbohydrates, particularly sodium, potassium, calcium or ammonium salts;

(a3) sugar alcohols, preferably naturally occurring sugar alcohols selected from the group consisting of glycerine, erythritol, threitol, arabitol, ribitol, xylitol, sorbitol, mannitol, maltitol, isomalt, dulcitol, lactitol, and the physiologically acceptable salts of these sugar alcohols, particularly sodium, potassium, calcium or ammonium salts;

(a4) naturally occurring sweeteners, preferably selected from the group consisting of (a4-1) miraculin, monellin, mabinlin, thaumatin, curculin, brazzein, pentaidin, D-phenylalanine, D-tryptophan, and extracts or fractions obtained from natural sources containing these amino acids and/or proteins, and the physiologically acceptable salts of these amino acids and/or proteins, particularly the sodium, potassium, calcium or ammonium salts;

(a4-2) neohesperidin dihydrochalcone, naringin dihydrochalcone, stevioside, steviolbioside, rebaudiosides, particularly rebaudioside A, rebaudioside B, rebaudioside C, rebaudioside D, rebaudioside E, rebaudioside F, rebaudioside G, rebaudioside H, dulcosides and rubusoside, suavioside A, suavioside B, suavioside G, suavioside H, suavioside I, suavioside J, baiyunoside 1 baiyunoside 2, phlomisoside 1, phlomisoside 2, phlomisoside 3, and phlomisoside 4, abrusoside A, abrusoside B, abrusoside C, abrusoside D, cyclocaryoside A and cyclocaryoside I, osladin, polypodoside A, strogin 1, strogin 2, strogin 4, selligueain A, dihydroquercetin-3-acetate, perillartine, telosmoside $A_{15}$, periandrin I-V, pterocaryosides, cyclocaryosides, mukuroziosides, trans-anethole, trans-cinnamaldehyde, bryosides, bryonosides, bryonodulcosides, carnosiflosides, scandenosides, gypenosides, trilobatin, phloridzin, dihydroflavanols, hematoxylin, cyanine, chlorogenic acid, albiziasaponin, telosmosides, gaudichaudioside, mogrosides, mogroside V, hernandulcins, monatin, phyllodulcin, glycyrrhetinic acid and derivatives thereof, particularly its glycosides such as glycyrrhizin, and the physiologically acceptable salts of these compounds, particularly the sodium, potassium, calcium or ammonium salts;

(a4-3) extracts or enriched fractions of extracts, selected from the group consisting of Thaumatococcus extracts (katemfe bush), extracts from *Stevia* ssp. (particularly *Stevia rebaudiana*), swingle extracts (*Momordica* or *Siratia grosvenorii*, Luo-Han-Guo), extracts from *Glycerrhyzia* ssp. (particularly *Glycerrhyzia glabra*), extracts from *Rubus* ssp. (particularly *Rubus suavissimus*), citrus extracts and extracts from *Lippia dulcis*;

(a5) synthetically sweet-tasting substances, preferably selected from the group consisting of magap, sodium cyclamate or other physiologically acceptable salts of cyclamic acid, acesulfame K or other physiologically acceptable salts, neohesperidin dihydrochalcone, naringin dihydrochalcone, saccharin, saccharin-sodium salt, aspartame, superaspartame, neotame, alitame, advantame, perillartine, sucralose, lugduname, carrelame, sucrononate and sucrooctate.

The flavourings in the above group (a1) cause or reinforce a sweet smell and/or taste impression and can be used as taste correctives.

Moreover, it has emerged from our own studies that the sweet taste impression of the aforementioned sweet-tasting substances can be particularly well reinforced by the extracts to be used according to the invention of *Mycetia balansae*.

In a preferred embodiment, the total amount of compounds of the formula (I) and the total amount of sweet-tasting substances of the above-defined groups (a4) and (a5) lie in the range of 0.001 to 1 wt %, preferably in the range of 0.001 to 0.5 wt %, further preferably in the range of 0.003 to 0.1 wt %, based on the total mass of the orally consumable formulation directly intended for consumption.

A preferred orally consumable formulation according to the invention comprises, besides a compound according to the invention and the physiologically acceptable salt thereof and/or the mixture thereof, additionally one or a plurality of further substances for reinforcing a sweet taste impression.

Further substances for reinforcing the sweet taste impression—without limiting the present invention thereto—are preferably selected from the group consisting of hydroxydeoxybenzoins such as, for example, 2-(4-hydroxy-3-methoxyphenyl)-1-(2,4,6-trihydroxyphenyl)ethanone, 1-(2,4-dihydroxyphenyl)-2-(4-hydroxy-3-methoxyphenyl)ethanone, 1-(2-hydroxy-4-methoxyphenyl)-2-(4-hydroxy-3- methoxyphenyl)ethanone) (particularly such as described in WO 2006/106023, which with reference to the corresponding compounds disclosed therein becomes a constituent part of this application in the manner of cross-referencing); hydroxyphenyl alkanedions such as, for example, isogingerdion-[2] (particularly such as described in WO 2007/003527, which with reference to the corresponding compounds disclosed therein becomes a constituent part of this application in the manner of cross-referencing); diacetyl trimers (particularly such as described in WO 2006/058893, which with reference to the corresponding compounds disclosed therein becomes a constituent part of this application in the manner of cross-referencing); divanillins (particularly such as described in WO 2004/078302, which with reference to the corresponding compounds disclosed therein becomes a constituent part of this application in the manner of cross-referencing); hesperetin as disclosed in WO 2007/014879, which with reference to these compounds becomes a constituent part of this application in the manner of cross-referencing, 4-hydroxydihydrochalcones, thereby particularly phloretin as disclosed in EP 1 998 636 B1, which with reference to these compounds becomes a constituent part of this application in the manner of cross-referencing, or propenylphenyl glycosides (chavicol glycosides) as described in EP 1 955 601 A1, which with reference to these compounds becomes a constituent part of this application in the manner of cross-referencing, hydroxyflavans as disclosed in EP 2 253 226 A1, which with reference to these compounds becomes a constituent part of this application in the manner of cross-referencing, certain extracts of *Hydrangea macrophylla* as disclosed in EP 2 298 084 A1, which with reference to these compounds becomes a constituent part of this application in the manner of cross-referencing, 1-(2,4-dihydroxyphenyl)-3-(3-hydroxy-4-methoxyphenyl)-propan-1-one as disclosed in the European patent application with the file no. 10152331.4 (Symrise), which with reference to these compounds becomes a constituent part of this application in the manner of cross-referencing.

In this arrangement, preferred sweet-taste reinforcing substances are particularly hesperetin, phloretin, 3',7-dihydroxy-4"-methoxyflavan and (S)-3',7-dihydroxy-4"-methoxyflavan, certain *hydrangea* extracts or phyllodulcin, and 1-(2,4-dihydroxyphenyl)-3-(3-hydroxy-4-methoxyphenyl)-propan-1-one.

Again, reinforcing effects with regard to the sweet impression of the formulations according to the invention can be achieved with the substances of the last-mentioned groups.

Furthermore, a formulation according to the invention is preferred, comprising one or a plurality of further aromatising plant extracts, flavouring, auxiliary or carrier substances.

Obviously, preferred formulations according to the invention also comprise further conventional food ingredients.

In preferred orally consumable formulations according to the invention, the total amount of compounds of the formula (I) is in the range of 0.01 ppm to 95 wt %, preferably in the range of 0.1 ppm to 90 wt %, preferably in the range of 1 ppm to 50 wt %, further preferably in the range of 1 ppm to 20 wt %, most particularly preferably in the range of 1 ppm to 5 wt %, based on the total mass of the formulation.

Very particularly preferred is an orally consumable formulation according to the invention, particularly an orally consumable formulation suitable for direct consumption, the total amount of compounds of the formula (I) being in the range of 0.01 ppm to 1000 ppm, preferably in the range of 0.1 ppm to 500 ppm, particularly preferably in the range of 1 to 100 ppm, based on the total weight of the formulation.

Even at very low concentrations, the sweet-reinforcing function of the compounds of the formula (I) can be utilised, as already indicated above, the reinforcing being synergistic, as also indicated above.

An orally consumable formulation according to the invention is preferred, this being selected from the group consisting of the pharmaceutical formulation, the mouth care formulation, the alimentary or stimulant liquid or solid food formulation and also cosmetic formulations for application in the region of the head which may come into contact with the oral cavity.

The formulations according to the invention can also be present in the form of a semi-finished product which is normally not directly orally consumed but is used to produce an orally consumable formulation according to the invention intended for direct consumption.

In this arrangement, semi-finished products according to the invention are used preferably in a concentration in the range of 0.0001 to 90 wt %, preferably in the range of 0.001 to 50 wt %, particularly preferably in the range of 0.01 to 20 wt %, based on the total mass of the resulting orally consumable formulation. Such semi-finished products can be present, e.g., as flavouring compositions.

Flavouring compositions within the meaning of the present invention contain besides one or a plurality of compounds of Formula (I), (II) and/or (III) and/or one or a plurality of the physiologically acceptable salts of these compounds at least (i) one, two, three, four, five, six, seven, eight, nine, ten or a plurality of (further) flavourings and/or (ii) one, two, three, four, five, six, seven or a plurality of (further) taste substances.

As already mentioned, the fresh or dried plant *Mycetia balansae* as such is not an object of the present invention. In contrast, an orally consumable formulation according to the invention can contain, besides one or a plurality of dried plant parts of *Mycetia balansae*, preferred plant parts in dried and comminuted form, additionally one or a plurality of further ingredients suitable for consumption, the further ingredients suitable for consumption preferably not being extractable from *Mycetia balansae* and preferably not being available in *Mycetia balansae*.

In this arrangement, a particularly preferable orally consumable formulation according to the invention is one that, besides one or a plurality of dried plant parts of *Mycetia balansae*, additionally contains one, two, three, four, five or a plurality of (further) flavourings, preferably selected from the above-defined group (a1) and/or the following defined group (A).

As already explained above, one aspect of the present invention relates to the use of a compound according to the invention of the formula (I), of a mixture according to the invention, or of an orally consumable formulation according to the invention in the form of a semi-finished product
  to achieve a sweet taste impression,
  to reinforce a sweet taste impression,
and/or
  as a taste corrective.

Accordingly, the invention also relates to the use of a compound according to the invention, preferably in one of the embodiments identified as preferred, and/or of a physiologically acceptable salt of a compound according to the invention, preferably in one of the embodiments identified as preferred, of a mixture according to the invention, preferably in one of the embodiments identified as preferred, or of an extract according to the invention, preferably in one of the embodiments identified as preferred, to generate a sweet impression in an orally consumable formulation or to reinforce the sweet impression of an orally consumable formulation comprising at least a further, preferably naturally occurring, sweet-tasting substance.

Orally consumable formulations can then be preferably sweet-tasting, alimentary, dietary supplement, mouth care or stimulant formulations, cosmetic formulations, preferably for application in the region of the head, or oral pharmaceutical formulations (i.e. pharmaceutical formulations intended for oral intake).

Flavouring compositions within the meaning of the invention can contain, besides the extracts of *Mycetia balansae* to be used according to the invention, one or a plurality of different natural or non-natural flavourings and/or aromatising foods, reaction flavours, flavour formulations, taste substances, further taste-modulating substances, precursors, other flavourings, additives, sweetening, colouring and acidifying agents, stabilisers and solvents, auxiliary and carrier substances.

Within the context of the present invention, (one or a plurality of) flavourings preferably to be used are preferably selected from the following group (A) consisting of: acetophenone, allyl capronate, alpha-ionone, beta-ionone, anisaldehyde, anisyl acetate, anisyl formate, benzaldehyde, benzothiazole, benzyl acetate, benzyl alcohol, benzyl benzoate, beta-ionone, butyl butyrate, butyl capronate, butylidenephthalide, carvone, camphene, caryophyllene, cineole, cinnamyl acetate, citral, citronellol, citronellal, citronellyl acetate, cyclohexyl acetate, cymol, damascone, decalactone, dihydrocoumarin, dimethyl anthranilate, dimethyl anthranilate, dodecalactone, ethoxyethyl acetate, ethyl butyric acid, ethyl butyrate, ethyl caprinate, ethyl capronate, ethyl crotonate, ethyl furaneol, ethyl guaiacol, ethyl isobutyrate, ethyl isovalerianate, ethyl lactate, ethyl methylbutyrate, ethyl propionate, eucalyptol, eugenol, ethyl heptylate, 4-(p-hydroxyphenyl)-2-butanone, gamma-decalactone, geraniol, geranyl acetate, geranyl acetate, grapefruit aldehyde, methyl dihydrojasmonate (e.g. Hedion®), heliotropin, 2-heptanone, 3-heptanone, 4-heptanone, trans-2-heptenal, cis-4-heptenal, trans-2-hexenal, cis-3-hexenol, trans-2-hexanoic acid, trans-3-hexanoic acid, cis-2-hexenyl acetate, cis-3-hexenyl acetate, cis-3-hexenyl capronate, trans-2-hexenyl capronate, cis-3-hexenyl formate, cis-2-hexyl acetate, cis-3-hexyl acetate, trans-2-hexyl acetate, cis-3-hexyl formate, para-hydroxybenzyl acetone, isoamyl alcohol, isoamyl isovalerianate, isobutyl butyrate, isobutyraldehyde, isoeugenol methyl ether, isopropyl methyl thiazole, lauric acid, leavulinic acid, linalool, linalool oxide, linalyl acetate, menthol, menthofuran, methyl anthranilate, methyl butanol, methyl butyric acid, 2-methylbutyl acetate, methyl capronate, methyl cinnamate, 5-methyl furfural, 3,2,2-methyl cyclopentenolone, 6,5,2-methyl heptenone, methyl dihydrojasmonate, methyl jasmonate, 2-methyl methylbutyrate, 2-methyl-2-pentenoic acid, methyl thiobutyrate, 3,1-methylthio hexanol, 3-methylthio hexyl acetate, nerol, neryl acetate, trans,trans-2,4-nonadienal, 2,4-nonadienol, 2,6-nonadienol, 2,4-nonadienol, nootkatone, delta octalactone, gamma octalactone, 2-octanol, 3-octanol, 1,3-octenol, 1-octyl acetate, 3-octyl acetate, palmitic acid, paraldehyde, phellandrene, pentanedione, phenylethyl acetate, phenylethyl alcohol, phenylethyl alcohol, phenylethyl isovalerianate, piperonal, propionaldehyde, propyl butyrate, pulegone, pulegol, sinensal, sulfurol, terpinene, terpineol, terpinolene, 8,3-thiomenthanone, 4,4,2-thiomethylpentanone, thymol, delta-undecalactone, gamma-undecalactone, valencene, valeric acid, vanillin, acetoin, ethyl vanillin, ethyl vanillin isobutyrate (=3-ethoxy-4-isobutyryloxybenzaldehyde), 2,5-dimethyl-4-hydroxy-3(2H)-furanone and derivatives thereof (here preferably homofuraneol (=2-ethyl-4-hydroxy-5-methyl-3(2H)-furanone), homofuronol (=2-ethyl-5-methyl-4-hydroxy-3(2H)-furanone and 5-ethyl-2-methyl-4-hydroxy-3(2H)-furanone), maltol and maltol derivatives (here preferably ethyl maltol), coumarin and coumarin derivatives, gamma-lactones (here preferably gamma-undecalactone, gamma-nonalactone, gamma-decalactone), delta-lactones (here preferably 4-methyl delta-decalactone, massoia lactone, delta-decalactone, tuberolactone), methyl sorbate, divanillin, 4-hydroxy-2(or 5)-ethyl-5(or 2)-methyl-3(2H) furanone, 2-hydroxy-3-methyl-2-cyclopentenone, 3-hydroxy-4,5-dimethyl-2(5H)-furanone, acetic acid isoamyl ester, butyric acid ethyl ester, butyric acid n-butyl ester, butyric acid isoamyl ester, 3-methyl-butyric acid ethyl ester, n-hexanoic acid ethyl ester, n-hexanoic acid allyl ester, n-hexanoic acid n-butyl ester, n-octanoic acid ethyl ester, ethyl-3-methyl-3-phenylglycidate, ethyl-2-trans-4-cis-decadienoate, 4-(p-hydroxyphenyl)-2-butanone, 1,1-dimethoxy-2,2,5-trimethyl-4-hexane, 2,6-dimethyl-5-hepten-1-al, phenyl acetaldehyde, 2-methyl-3-(methylthio)furan, 2-methyl-3-furanthiol, bis(2-methyl-3-furyl)disulfide, furfuryl mercaptan, methional, 2-acetyl-2-thiazoline, 3-mercapto-2-pentanone, 2,5-dimethyl-3-furanthiol, 2,4,5-trimethylthiazole, 2-acetylthiazole, 2,4-dimethyl-5-ethylthiazole, 2-acetyl-1-pyrroline, 2-methyl-3-ethylpyrazine, 2-ethyl-3,5-dimethylpyrazine, 2-ethyl-3,6-dimethylpyrazine, 2,3-diethyl-5-methylpyrazine, 3-isopropyl-2-methoxypyrazine, 3-isobutyl-2-methoxypyrazine, 2-acetylpyrazine, 2-pentylpyridine, (E,E)-2,4-decadienal, (E,E)-2,4-nonadienal, (E)-2-octenal, (E)-2-nonenal, 2-undecenal, 12-methyl tridecanal, 1-penten-3-one, 4-hydroxy-2,5-dimethyl-3(2H)-furanone, guaiacol, 3-hydroxy-4,5-dimethyl-2(5H)-furanone, 3-hydroxy-4-methyl-5-ethyl-2(5H)-furanone, cinnamaldehyde, cinnamyl alcohol, methyl salicylate, isopulegol and (not explicitly listed here) stereoisomers, enantiomers, position isomers, diastereomers, cis/trans-isomers and epimers of these substances.

In a preferred embodiment, the total amount of a flavouring composition according to the invention, preferably containing one, two, three, four, five or a plurality of the flavourings from the above-defined group (a1) and/or the group (A), is in the range of 0.01 to 1 wt %, preferably in the range of 0.01 to 0.5 wt %, further preferably in the range of 0.01 to 0.1 wt %, based on the total mass of the orally consumable formulation directly intended for consumption.

The liquid and solid alimentary or stimulant food formulation within the meaning of the invention is, e.g. baked goods (e.g. bread, biscuits, cake, other baked goods), confectionery in the narrower sense (e.g. chocolates, chocolate bar products, other bar products, fruit gums, hard and soft candies, chewing gum), alcoholic or non-alcoholic beverages (e.g. coffee, tea, wine, wine-containing beverages, beer, beer-containing beverages, liqueurs, spirits, brandies, fruit-containing lemonades, isotonic drinks, soft drinks, nectars, fruit and vegetable juices, fruit or vegetable juice formulations), instant beverages (e.g. instant cocoa drinks, instant tea drinks, instant coffee drinks), meat products (e.g. ham, cold cuts sausage or cured sausage formulations, spiced or marinated raw or salted meat products), eggs or egg products (dried egg, egg white, egg yolk), grain products (e.g. breakfast cereals, muesli bars, pre-cooked ready-to-eat rice products), milk products (e.g. milk drinks, milk ice-cream, yoghurt, kefir, cottage cheese, soft cheese, hard cheese, dried milk powder, whey, butter, buttermilk, partially or wholly hydrolysed milk protein-containing products), products from soya protein or other soya bean fractions (e.g. soya milk and products made therefrom, soya lecithin-containing formulations, fermented products such as tofu or tempeh or products made therefrom, soya sauces), fruit formulations (e.g. jams, sorbets, fruit sauces, fruit fillings), vegetable formulations (e.g. ketchup, sauces, dried vegetables, frozen vegetables, pre-cooked vegetables, vinegar-pickled vegetables, bottled vegetables), snacks (e.g. baked or fried potato crisps or potato dough products, bread dough products, extrudates based on maize or peanut), fat and oil-based products or emulsions thereof (e.g. mayonnaise, remoulade, dressings, spice formulations), other ready-made meals and soups (e.g. dried soups, instant soups, pre-cooked soups), spices, seasoning blends and particularly seasonings which find a use, for example, in the snack sector.

The formulations within the meaning of the invention can also be present as dietary supplements in the form of capsules, tablets (uncoated and coated tablets, e.g. gastro-resistant coatings), sugar-coated pills, granulates, pellets, solid mixtures, dispersions in liquid phases, as emulsions, as powders, as solutions, as pastes or as other formulations that can be swallowed or chewed.

Mouth care formulations (oral hygiene products) within the meaning of the present invention are particularly mouth and/or dental hygiene products such as toothpastes, tooth gels, tooth powders, mouthwashes, chewing gums and other mouth care products.

Oral pharmaceutical formulations within the meaning of the invention are formulations which are present, e.g., in the form of capsules, tablets (uncoated and coated tablets, e.g. gastro-resistant coatings), sugar-coated pills, granulates, pellets, solid mixtures, dispersions in liquid phases, as emulsions, as powders, as solutions, as pastes or as other formulations that can be swallowed or chewed, and are used as prescription-only, over-the-counter or other medicines or as dietary supplements.

Cosmetic formulations for application in the region of the head are particularly those which, even if correctly applied to the skin, may come into contact with the oral cavity; for example, as already mentioned, cosmetic formulations for application in the region of the head such as soaps, other cleansing or care products for the facial area, face creams, face lotions or face ointments, sun protection products, beard cleaning or care products, shaving foams, shaving soaps or shaving gels, lipsticks or other lip cosmetics or lip care products.

Further conventional active, parent, auxiliary and additive substances for orally consumable formulations according to the invention can be contained in amounts from up to 99.999999 wt %, preferably 10 to 80 wt %, based on the total weight of the formulation. In this arrangement, the orally consumable formulations according to the invention can preferably contain water in an amount up to 99.999999 wt %, preferably 1 to 95 wt %, preferably 5 to 80 wt %, based on the total weight of the formulation.

The formulations according to the invention containing extracts of *Mycetia balansae* are produced according to a preferred embodiment in which the extracts of *Mycetia balansae* are preferably incorporated into an orally consumable base formulation as a flavouring composition in the form of a mixture with a solid or liquid carrier substance. Preferably, formulations according to the invention that are present as a solution can also be converted to a solid formulation by spray drying.

According to a further preferred embodiment, for the production of orally consumable formulations according to the invention, the extracts of *Mycetia balansae* or flavouring compositions containing these are also incorporated in advance into emulsions, into liposomes, e.g. starting from phosphatidylcholine, into microspheres, into nanospheres or also into capsules, granulates or extrudates from a matrix suitable for foods and stimulants, e.g. from starch, starch derivatives, cellulose or cellulose derivatives (e.g. hydroxypropyl cellulose), other polysaccharides (e.g. alginate), natural fats, natural waxes (e.g. beeswax, carnauba wax) or from proteins, e.g. gelatine.

In a further preferred production method, the extracts of *Mycetia balansae* or flavouring compositions containing these are complexed in advance with one or a plurality of suitable sequestrants, for example, with cyclodextrins or cyclodextrin derivatives, preferably α- or β-cyclodextrin, and used in this complexed form.

Particularly preferred is an orally consumable formulation according to the invention in which the matrix is selected so that the extracts of *Mycetia balansae* or, more precisely, the balansins of the formula (I) are slow-released from the matrix so that a sustained effect is obtained.

Conventional parent, auxiliary and additive substances for foods or stimulants can be used as further ingredients for orally consumable formulations according to the invention, e.g. water, mixtures of fresh or processed, vegetable or animal parent substances or starting materials (e.g. raw, roast, dried, fermented, smoked and/or cooked meat, bones, gristle, fish, vegetables, fruit, herbs, nuts, vegetable or fruit juices or pastes or mixtures thereof), digestible or indigestible, non-sweet carbohydrates (e.g. dextrins, amylose, amylopectin, inulin, xylans, cellulose), natural or hardened fats (e.g. suet, lard, palm oil, coconut oil, hardened vegetable fat), oils (e.g. sunflower oil, peanut oil, corn oil, olive oil, fish oil, soya oil, sesame oil), fatty acids or salts thereof (e.g. potassium stearate), proteinogenic or non-proteinogenic amino acids and related compounds (e.g. γ-aminobutyric acid, taurine), peptides (e.g. glutathione), native or processed proteins (e.g. gelatines), enzymes (e.g. peptidases), nucleic acids, nucleotides, other taste correctives for unpleasant taste impressions, taste modulators for further, generally not unpleasant taste impressions, further taste-modulating substances (e.g. inositol phosphate, nucleotides such as guanosine monophosphate, adenosine monophosphate or other substances such as sodium glutamate or 2-phenoxypropionic acid), emulsifiers (e.g. lecithins, diacylglycerols, gum arabic), stabilisers (e.g. carrageenan, alginate), preservatives (e.g. benzoic acid, sorbic acid), antioxidants (e.g. tocopherol, ascorbic acid), chelators (e.g. citric acid), organic or inorganic acidifying agents (e.g. malic acid, acetic acid, citric acid, tartaric acid, phosphoric acid), additional bitter principles (e.g. quinine, caffeine, limonene, amarogentin, humolones, lupolones, catechins, tannins), mineral salts (e.g. sodium chloride, potassium chloride, magnesium chloride, sodium phosphates), substances preventing enzymatic browning (e.g. sulfite, ascorbic acid), essential oils, plant extracts, natural or synthetic colourings or colouring pigments (e.g. carotenoids, flavonoids, anthocyanins, chlorophyll and derivatives thereof), spices, trigeminally active substances or plant extracts containing such trigeminally active substances, synthetic, natural or nature-identical flavourings or scents and odour correctives.

Dental hygiene products (as basis for mouth care formulations) generally comprise an abrasive system (grinding or polishing agent) such as, e.g., silicic acids, calcium carbonates, calcium phosphates, aluminium oxides and/or hydroxylapatites, surfactant substances such as, e.g., sodium lauryl sulfate, sodium lauryl sarcosinate and/or cocamidopropyl betaine, humectants such as, e.g., glycerine and/or sorbite, thickeners such as, e.g., carboxymethyl cellulose, polyethylene glycols, carrageenan and/or Laponite®, taste correctives for unpleasant taste impressions, taste correctives for further, generally not unpleasant taste impressions, taste-modulating substances (e.g. inositol phosphate, nucleotides such as guanosine monophosphate, adenosine monophosphate or other substances such as sodium glutamate or 2-phenoxypropionic acid), coolants such as, e.g., menthol, menthol derivatives (e.g. L-menthol, L-menthyl lactate, L-menthylalkyl carbonates, menthone ketals, menthane carboxylic acid amides), 2,2,2-trialkyl acetamides (e.g. 2,2-diisopropylpropionic acid methylamide), icilin derivatives, stabilisers and active substances such as, e.g., sodium fluoride, sodium monofluorophosphate, tin(II)fluoride, quaternary ammonium fluorides, zinc citrate, zinc sulfate, stannous pyrophosphate, tin(II)chloride, mixtures of different pyrophosphates, triclosan, cetylpyridinium chloride, aluminium lactate, potassium citrate, potassium nitrate, potassium chloride, strontium chloride, hydrogen peroxide, flavours and/or sodium carbonate or odour correctives.

Chewing gums (as a further example of mouth care formulations) generally comprise a chewing gum base, i.e. a chewing mass that becomes plastic when chewed, other taste correctives for unpleasant taste impressions, taste modulators for further, generally not unpleasant taste impressions, taste-modulating substances (e.g. inositol phosphate, nucleotides such as guanosine monophosphate, adenosine monophosphate or other substances such as sodium glutamate or 2-phenoxypropionic acid), humectants, thickeners, emulsifiers, further flavours and stabilisers or odour correctives.

All conventional further active, parent, auxiliary and additive substances for oral pharmaceutical formulations can be used as ingredients for oral pharmaceutical formulations according to the invention. Particularly, even unpleasant-tasting orally formulatable active pharmaceutical substances can be used as active substances. The active, parent, auxiliary and additive substances can be converted to the oral application forms in a manner as known per se. This occurs regularly by using inert, non-toxic, pharmaceutically suitable auxiliary substances. Among others, they include carrier substances (e.g. microcrystalline cellulose), solvents (e.g. liquid polyethylene glycols), emulsifiers (e.g. sodium dodecyl sulfate), dispersants (e.g. polyvinyl pyrrolidone), synthetic and natural biopolymers (e.g. albumin), stabilisers (e.g. antioxidants such as ascorbic acid), colourings (e.g. inorganic pigments such as iron oxides) and odour correctives as well as taste correctives not relating to bitter taste.

Preferably, the orally consumable formulations according to the invention can also contain a further flavour composition in order to round off and refine the taste and/or smell of the formulation. Suitable flavour compositions contain, e.g., synthetic, natural or nature-identical flavour, scent and/or taste substances as well as suitable auxiliary and carrier substances. It is considered particularly preferable here that a potentially existing bitter or metallic taste impression emanating from flavour, scent and/or taste substances contained in the formulations according to the invention can be reduced or suppressed, thus improving the overall flavour or taste profile.

Semi-finished products according to the invention can be used to reinforce the sweet taste impression of orally consumable finished goods (i.e. of formulations intended for direct consumption) which are produced using the semi-finished product according to the invention.

Semi-finished products according to the invention preferably contain the compounds of the formula (I) or a plant extract according to the invention, preferably of *Mycetia balansae*, in a total amount in the range of 0.001 to 99 wt %, preferably in the range of 1 to 95 wt %, further preferably in the range of 5 to 95 wt %, particularly preferably in the range of 10 to 95 wt %, based on the total weight of the semi-finished product.

Formulations to be used according to the invention, which are present as semi-finished products, can be used to achieve and/or reinforce the sweet taste impression of finished product formulations that are produced using the semi-finished product formulation.

In a particularly preferred embodiment of the invention, a formulation according to the invention comprises, besides a compound according to the invention of the formula (I), a physiologically acceptable salt of a compound of the formula (I), a mixture according to the invention or an extract according to the invention, one or a plurality of taste correctives, i.e. one or a plurality of further substances that do not correspond to the formula (I), the taste corrective(s) being suitable for changing or masking (here, masking means reducing or completely suppressing) the unpleasant taste impression of one or more unpleasant tasting substances, or reinforcing a pleasant taste impression, preferably a further taste impression in addition to a sweet taste impression, or reinforcing a pleasant-tasting substance, preferably a pleasant-tasting substance which, in addition to a sweet taste impression, imparts a further pleasant taste impression.

Unpleasant taste impressions within the meaning of the present invention are here:
bitter, astringent, very hot, pungent, sticky, chalky, dusty, dry, floury, rancid, extremely sour and/or metallic and
a corresponding (if applicable, strongly lingering) aftertaste.

Pleasant taste impressions (except or in addition to a sweet taste impression) within the meaning of the present invention are here:
oily, umami, spicy, mildly warming, pleasantly cooling, creamy, kokumi The further taste correctives can be selected preferably from the following list: nucleotides (e.g. adenosine-5'-monophosphate, cytidine-5'-monophosphate) or pharmaceutically acceptable salts thereof, lactisoles, sodium salts (e.g. sodium chloride, sodium lactate, sodium citrate, sodium acetate, sodium gluconoate), hydroxyflavanones such as, for example, eriodictyol, sterubin (eriodictyol-7-methylether), homoeriodictyol and sodium, potassium, calcium, magnesium or zinc salts thereof (particularly those as described in EP 1 258 200 A2, which with reference to the corresponding compounds disclosed therein becomes a constituent part of this application in the manner of cross-referencing), hydroxybenzoic acid amides such as, for example, 2,4-dihydroxybenzoic acid vanillyl amide, 2,4-dihydroxybenzoic acid-N-(4-hydroxy-3-methoxybenzyl)amide, 2,4,6-trihydroxybenzoic acid-N-(4-hydroxy-3-methoxybenzyl) amide, 2-hydroxy-benzoic acid-N-4-(hydroxy-3-methoxybenzyl)amide, 4-hydroxybenzoic acid-N-(4-hydroxy-3-methoxybenzyl)amide, 2,4-dihydroxybenzoic acid-N-(4-hydroxy-3-methoxybenzyl)amide-monosodium salt, 2,4-dihydroxybenzoic acid-N-2-(4-hydroxy-3-methoxyphenyl)ethylamide, 2,4-dihydroxybenzoic acid-N-(4-hydroxy-3-ethoxybenzyl)amide, 2,4-dihydroxybenzoic acid-N-(3,4-dihydroxybenzyl)amide and 2-hydroxy-5-methoxy-N-[2-(4-hydroxy-3-methoxyphenyl)ethyl]amide; 4-hydroxybenzoic acid vanillyl amide (particularly those as described in WO 2006/024587, which with reference to the corresponding compounds disclosed therein becomes a constituent part of this application in the manner of cross-referencing); hydroxydeoxybenzoins such as, for example, 2-(4-hydroxy-3-methoxyphenyl)-1-(2,4,6-trihydroxyphenyl)ethanone, 1-(2,4-dihydroxyphenyl)-2-(4-hydroxy-3-methoxyphenyl)ethanone, 1-(2-hydroxy-4-methoxyphenyl)-2-(4-hydroxy-3-methoxyphenyl)ethanone) (particularly those as described in WO 2006/106023, which with reference to the corresponding compounds disclosed therein becomes a constituent part of this application in the manner of cross-referencing); hydroxyphenyl alkanedions such as, for example, gingerdion-[2], gingerdion-[3], gingerdion-[4], dihydrogingerdion-[2], dihydrogingerdion-[3], dihydrogingerdion-[4], (particularly those as described in WO 2007/003527, which with reference to the corresponding compounds disclosed therein becomes a constituent part of this application in the manner of cross-referencing); diacetyl trimers (particularly those as described in WO 2006/058893, which with reference to the corresponding compounds disclosed therein becomes a constituent part of this application in the manner of cross-referencing); γ-amino butyric acids (particularly those as described in WO 2005/096841, which with reference to the corresponding compounds disclosed therein becomes a constituent part of this application in the manner of cross-referencing); divanillins (particularly such as described in WO 2004/078302, which with reference to the corresponding compounds disclosed therein becomes a constituent part of this application in the manner of cross-referencing) and 4-hydroxydihydrochalcones, preferably as described in US 2008/227867 A1, which with reference to the corresponding compounds disclosed therein becomes a constituent part of this application in the manner of cross-referencing, here, particularly phloretin and davidigenin, amino acids or mixtures of whey proteins with lecithins, hesperetin as disclosed in WO 2007/014879, which with reference to these compounds becomes a constituent part of this application in the manner of cross-referencing, 4-hydroxydihydrochalcones, as disclosed in WO 2007/107596, which with reference to these compounds becomes a constituent part of this application in the manner of cross-referencing, or propenylphenyl glycosides (chavicol glycosides) as described in EP 1 955 601 A1, which with reference to these compounds becomes a constituent part of this application in the manner of cross-referencing, pellitorine, particularly trans-pellitorine, and flavour compositions derived therefrom as described in EP 2 008 530 A1, which with reference to these compounds and flavour compositions become a constituent part of this application in the manner of cross-referencing, certain extracts from Rubus suavissimus as described in U.S. Provisional Application 61/333,435 (Symrise) and the patent applications based on it (e.g. the European patent application with the File no. 11165566.8 (Symrise)), which with reference to these extracts become a constituent part of this application in the manner of cross-referencing, umami compounds as described in WO 2008/046895 A1 and EP 1 989 944 A1, which each with reference to these compounds become a constituent part of this application in the manner of cross-referencing, and umami compounds as described in EP 2 064 959 A1 and EP 2 135 516 A1, which with reference to the corresponding compounds disclosed therein become a constituent part of this application in the manner of cross-referencing, phyllodulcin or extracts of Hydrangea macrophylla var. thunbergii makino and flavour compositions derived therefrom as described in EP 2 298 084 A1 and US 2011/0076239 A1, which with reference to these extracts or, more precisely, phyllodulcin become a constituent part of this application in the manner of cross-referencing, hydroxyflavan derivatives and flavour compositions derived therefrom, as described in US 2010/0292175 A1, which with reference to these compounds and the flavour compositions derived therefrom become a constituent part of this application in the manner of cross-referencing.

If a formulation according to the invention contains, for example, a comparatively high concentration of a compound according to the invention of the formula (I), of a physiologically acceptable salt of a compound of the formula (I), of a mixture according to the invention or of an extract according to the invention, it can happen that, besides the described desired sensory effects, additionally undesirable and even unpleasant taste impressions occur such as, for example, bitter notes. These undesirable and/or unpleasant taste impressions can be at least partially reduced or even fully suppressed by taste correctives.

Thus, the invention in a preferred embodiment also relates to a formulation according to the invention, containing (a) a compound according to the invention of the formula (I), a physiologically acceptable salt of a compound of the formula (I), a mixture according to the invention or an extract according to the invention, and (b) one or a plurality of (further) substances for masking an unpleasant taste impression, particularly a bitter, extremely sour or astringent taste impression.

Preferably, in this arrangement, one or a plurality of substances of the ingredient (b) are selected from the group consisting of sodium salts (here, preferably sodium chloride, sodium lactate, sodium citrate, sodium acetate, sodium gluconate), homoeriodictyol or sodium salts thereof, eriodictyol, trans-pellitorine and rubus extracts, preferably rubus extracts as described in the European patent application with the File no. 11165566.8 (Symrise).

EXAMPLES

The examples serve only to clarify the invention without thereby limiting it. Unless otherwise indicated, all data relate to the weight.

Example 1

Mycetia balansae Extract by Consecutive Extraction

Dried and ground above-ground plant parts of Mycetia balansae (100 g) were extracted twice consecutively with 1 L heptane, methylene chloride, tert-butyl methyl ether, ethyl acetate and ethanol/water (4:1) (parts by volume; v/v) in increasing polarity under agitation at room temperature for 1 h each. In this context, consecutively means that the plant material was treated in the cited sequence with the respective extractant, whereby the respective extractant was drained off and the then already extracted plant material was subjected to the next extractant in the next extraction step. The extractant was removed under vacuum, and the obtained dried extracts were tasted and sensorily evaluated in a dose of 500 ppm in a sugar solution (5%).

| Extractant | Yield (wt % based on the total weight of the leaves) | Content (wt %) of Balansin A and Balansin B* | Taste description |
| --- | --- | --- | --- |
| Heptane | 0.3 | not detectable | herbaceous, bitter |
| Methylene chloride | 0.25 | not detectable | earthy, musty, bitter, smoky |
| tert-Butyl methyl ether | 0.2 | not detectable | bitter, astringent, smoky, fleshy |
| Ethyl acetate | 0.12 | Balansin A 3.8% | sweetener, bitter, sticky, herbaceous |
| Ethanol/water (4:1) (v/v) | 4.7 | Balansin A 4.6% Balansin B 4.5% | sweetener, sweet, floral, slightly fruity, weakly bitter |

*quantification by LC/MS against an internal standard

Due to the pleasant taste, the removal of the unpleasant taste by the preceding extraction with less polar extractants and the markedly higher yield, the ethanol/water extract was selected for further tests.

Example 2

Enriched *Mycetia balansae* Extract

The ethanolic-aqueous extract described in Example 1 was dissolved in a concentration of 250 mg/ml in ethanol/water (1:2) (v/v) for separation by high temperature-liquid chromatography (HTLC). 100 μl of this solution was injected and fractionated through a polymer column (PS-DVB, Hamilton PRP-1; 250×10 mm) at 120° C. (isothermal). The gradient described below was used:

| t [min] | Water [%] | Ethanol [%] |
| --- | --- | --- |
| 0.0 | 100 | 0 |
| 25.0 | 75 | 25 |
| 40.0 | 0 | 100 |
| 50.0 | 0 | 100 |

The eluate was cut into 12 fractions of 4 minutes each and analysed by LC-MS. After removing the eluent, the fractions were each taken up in 2 ml water and sensorily evaluated by a trained panel.

Fraction 9, which contains among others the two compounds Balansin A and B according to the invention, was described by the testers of this panel as markedly sweet, like a sweetener and liquorice.

The LC-MS chromatogram of Fraction 9 containing Balansin A and Balansin B is presented in FIG. 1. In FIG. 1, the top diagram [a] shows the negative mode mass spectrum, the middle diagram [b] the positive mode mass spectrum and the bottom diagram [c] the UV spectrum.

Example 3

Producing an Aqueous/Ethanolic *Mycetia balansae* Extract 200 g dried leaves of *Mycetia balansae* were each extracted 4× exhaustively with 2 liters of an ethanol/water mixture in the ratio (4:1) (v/v) for 1 hour each at room temperature (approx. 23° C.). After filtration, the extractant was removed under vacuum. The yield of dry extract subsequently determined was 18.23 g; the content of Balansin A was 5.8%, the content of Balansin B was 5.7%, with the quantification being performed by LC/MS against an internal standard.

Example 4

Isolation of Balansin A and Balansin B from *Mycetia balansae* Extract

Isolation of the compounds Balansin A and Balansin B was performed by preparative high performance chromatography (pHPLC). For this purpose, the ethanolic-aqueous extract in the 150 mg/ml concentration was dissolved in a water/acetonitrile mixture (1:1) (v/v). Separation was carried out through a Grom Saphir 110 C-18 column (5 μm, 150×20 mm; pre-column 10×20 mm; injection volume 1000 μl). Elution was performed isocratically with a water/acetonitrile mixture (7:3) (v/v) at a flowrate of 25 ml/min and a detection at 210 nm.

The fractions from 50 cycles were collected in the range of 10.5 to 13.0 min (Balansin B) and in the range of 19.5 to 23.0 min (Balansin A) and liberated from the solvent in the rotary evaporator at 40° C. and 0.1 mbar. The yield of Balansin A was 180 mg and the yield of Balansin B was 230 mg.

| Substance | Empirical formula | Mass | m/z | UV maximum |
| --- | --- | --- | --- | --- |
| Balansin A | $C_{42}H_{71}O_{14}$ | 799.4824 | 711.4, 637.4, 549.4, 221.1, 179.1, 161.0, 143.0, 113.0, 101.0 | 200 nm |
| Balansin B | $C_{48}H_{81}O_{19}$ | 961.5421 | 799.5, 711.4, 637.4, 549.4, 221.1, 179.1, 161.0, 143.0, 113.0, 101.0 | 200 nm |

Example 5

Characterisation of Balansin A by NMR Spectroscopy

For the structure elucidation of the isolated compound Balansin A from Example 4, different methods of one- and two-dimensional $^1$H- and $^{13}$C-NMR spectroscopy were carried out. The data obtained thereby are listed as follows.

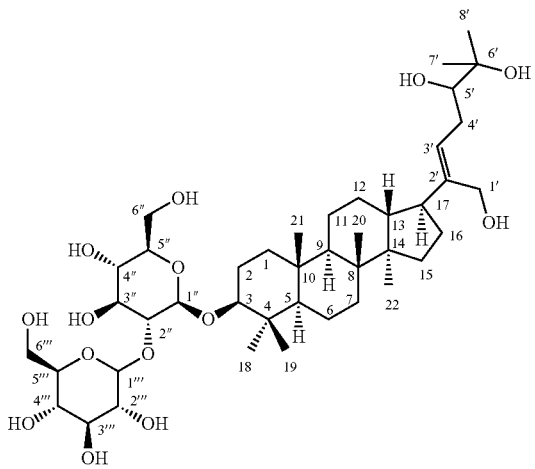

¹H-NMR; CD₃OD, TMS; 600 MHz

| C | δ in ppm | Multiplicity | Number of H | J in Hz |
|---|---|---|---|---|
| 1a | 1.71 | m | 1 | |
| 1b | 1.00 | m | 1 | |
| 2a | 1.96 | m | 1 | |
| 2b | 1.71 | m | 1 | |
| 3 | 3.24 | m | 1 | |
| 5 | 0.78 | d | 1 | 11.5 |
| 6a | 1.56 | m | 1 | |
| 6b | 1.48 | m | 1 | |
| 7a | 1.62 | m | 1 | |
| 7b | 1.30 | m | 1 | |
| 9 | 1.36 | m | 1 | |
| 11a | 1.54 | m | 1 | |
| 11b | 1.25 | m | 1 | |
| 12a | 1.64 | m | 1 | |
| 12b | 1.07 | m | 1 | |
| 13 | 1.77 | d, d, d | 1 | 3.3, 12.2, 12.2 |
| 15a | 1.64 | m | 1 | |
| 15b | 1.12 | m | 1 | |
| 16a | 1.90 | m | 1 | |
| 16b | 1.41 | m | 1 | |
| 17 | 2.30 | d, d, d | 1 | 6.8, 11.0, 11.0 |
| 18 | 1.07 | s | 3 | |
| 19 | 0.85 | s | 3 | |
| 20 | 1.02 | s | 3 | |
| 21 | 0.89 | s | 3 | |
| 22 | 0.91 | s | 3 | |
| 1'a | 4.13 | d | 1 | 11.7 |
| 1'b | 3.90 | d | 1 | 11.7 |
| 3' | 5.44 | d, d | 1 | 6.9 8.7 |
| 4'a | 2.39 | d, d, d | 1 | 2.4, 6.5, 14.4 |
| 4'b | 2.20 | d, d, d | 1 | 8.9, 10.3, 14.4 |
| 5' | 3.24 | m | 1 | |
| 7' | 1.18 | s | 3 | |
| 8' | 1.16 | s | 3 | |
| 1" | 4.43 | d | 1 | 7.5 |
| 2" | 3.57 | m | 1 | |
| 3" | 3.35 | d, d | 1 | 8.6, 9.3 |
| 4" | 3.15-3.29 | m | 1 | |
| 5" | 3.15-3.29 | m | 1 | |
| 6"a | 3.85 | d, d | 1 | 2.0, 12.0 |
| 6"b | 3.65, | d, d | 1 | 5.5, 12.0 |
| 1''' | 4.67 | d | 1 | 7.7 |
| 2''' | 3.15-3.29 | m | 1 | |
| 3''' | 3.56 | m | 1 | |
| 4''' | 3.15-3.29 | m | 1 | |
| 5''' | 3.15-3.29 | m | 1 | |
| 6'''a | 3.82 | d, d | 1 | 2.3, 11.9 |
| 6'''b | 3.61 | d, d | 1 | 6.4, 11.9 |

¹³C-shift values 125 MHz, CD₃OD

| C | δ in ppm | Multiplicity |
|---|---|---|
| 1 | 40.49 | T |
| 2 | 27.36 | T |
| 3 | 91.50 | D |
| 4 | 40.69 | S |
| 5 | 57.72 | D |
| 6 | 19.31 | T |
| 7 | 36.72 | T |
| 8 | 41.79 | S |
| 9 | 52.45 | D |
| 10 | 38.15 | S |
| 11 | 22.57 | T |
| 12 | 26.05 | T |
| 13 | 46.83 | D |
| 14 | 50.37 | S |
| 15 | 32.67 | T |
| 16 | 29.56 | T |
| 17 | 49.60 | D |
| 18 | 28.43 | Q |
| 19 | 16.79 | Q |
| 20 | 16.24 | Q |
| 21 | 16.88 | Q |
| 22 | 16.35 | Q |
| 1' | 58.94 | T |
| 2' | 144.38 | S |
| 3' | 127.82 | D |
| 4' | 30.94 | T |
| 5' | 78.70 | D |
| 6' | 73.87 | S |
| 7' | a 26.02 | Q |
| 8' | a 24.78 | Q |
| 1" | 105.45 | D |
| 2" | 81.08 | D |
| 3" | b 78.57 | D |
| 4" | c 71.98 | D |
| 5" | b 78.41 | D |
| 6" | 62.90 | T |
| 1''' | 104.54 | D |
| 2''' | 76.35 | D |
| 3''' | b 77.94 | D |
| 4''' | c 71.65 | D |
| 5''' | b 77.74 | D |
| 6''' | 63.18 | T |

Example 6

Characterisation of Balansin B by NMR Spectroscopy

For the structure elucidation of the isolated compound Balansin A from Example 4, different methods of one- and two-dimensional ¹H- and ¹³C-NMR spectroscopy were carried out. The data obtained thereby are listed as follows.

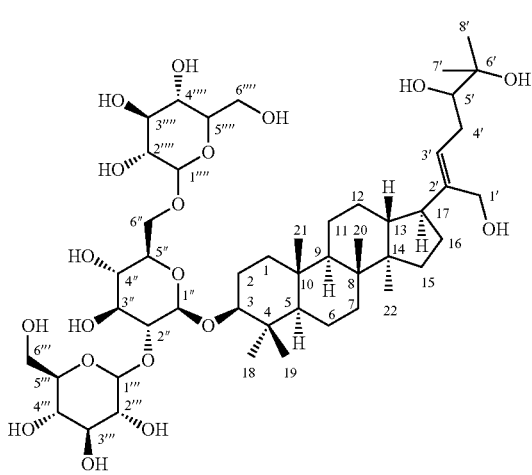

¹H-NMR; CD₃OD, TMS; 600 MHz

| C | δ in ppm | Multiplicity | Number of H | J in Hz |
|---|---|---|---|---|
| 1a | 1.72 | m | 1 | |
| 1b | 1.02 | m | 1 | |
| 2a | 1.95 | m | 1 | |
| 2b | 1.71 | m | 1 | |
| 3 | 3.23 | m | 1 | |
| 5 | 0.79 | d, d | 1 | 1.7, 11.6 |
| 6a | 1.56 | m | 1 | |
| 6b | 1.49 | d, d, d | 1 | 2.4, 12.6, 12.6 |
| 7a | 1.62 | m | 1 | |
| 7b | 1.31 | m | 1 | |
| 9 | 1.37 | d, d | 1 | 2.7, 12.8 |
| 11a | 1.56 | m | 1 | |
| 11b | 1.24 | m | 1 | |
| 12a | 1.63 | m | 1 | |
| 12b | 1.07 | m | 1 | |
| 13 | 1.77 | d, d, d | 1 | 3.5, 12.0, 12.0 |
| 15a | 1.65 | m | 1 | |
| 15b | 1.13 | m | 1 | |
| 16a | 1.90 | d, d, d, d | 1 | 8.8, 8.8, 10.1, 13.4 |
| 16b | 1.41 | m | 1 | |
| 17 | 2.30 | d, d, d | 1 | 6.9, 10.6, 10.6 |
| 18 | 1.07 | s | 3 | |
| 19 | 0.85 | s | 3 | |
| 20 | 1.02 | s | 3 | |
| 21 | 0.89 | s | 3 | |
| 22 | 0.91 | s | 3 | |
| 1'a | 4.13 | d | 1 | 11.5 |
| 1'b | 3.91 | d | 1 | 11.5 |
| 3' | 5.44 | d, d | 1 | 6.8, 8.6 |
| 4'a | 2.39 | d, d, d | 1 | 2.1, 6.7, 14.3 |
| 4'b | 2.20 | d, d, d | 1 | 8.9, 10.0, 14.3 |
| 5' | 3.23 | m | 1 | |
| 7' | 1.18 | s | 3 | |
| 8' | 1.16 | s | 3 | |
| 1" | 4.45 | d | 1 | 7.5 |
| 2" | 3.58 | m | 1 | |
| 3" | 3.55 | d, d | 1 | 8.8, 8.8 |
| 4" | 3.35 | m | 1 | |
| 5" | 3.46 | d, d, d | 1 | 2.0, 5.9, 9.9 |
| 6"a | 4.12 | d, d | 1 | 1.9, 11.8 |
| 6"b | 3.78 | d, d | 1 | 5.9, 11.8 |
| 1''' | 4.67 | d | 1 | 7.7 |
| 2''' | 3.17-3.29 | m | 1 | |
| 3''' | 3.17-3.29 | m | 1 | |
| 4''' | 3.17-3.29 | m | 1 | |
| 5''' | 3.17-3.29 | m | 1 | |
| 6'''a | 3.82 | d, d | 1 | 2.4, 11.8 |
| 6'''b | 3.61 | d, d | 1 | 6.1, 11.8 |
| 1'''' | 4.39 | d | 1 | 7.9 |
| 2'''' | 3.17-3.29 | m | 1 | |
| 3'''' | 3.17-3.29 | m | 1 | |
| 4'''' | 3.17-3.29 | m | 1 | |
| 5'''' | 3.17-3.29 | m | 1 | |
| 6''''a | 3.86 | d, d | 1 | 2.1, 11.9 |
| 6''''b | 3.66 | d, d | 1 | 5.4, 11.9 |

¹³C-NMR, 125 MHz, CD₃OD

| C | δ in ppm | Multiplicity |
|---|---|---|
| 1 | 40.48 | T |
| 2 | 27.44 | T |
| 3 | 91.45 | D |
| 4 | 40.71 | S |
| 5 | 57.68 | D |
| 6 | 19.33 | T |
| 7 | 36.71 | T |
| 8 | 41.79 | S |
| 9 | 52.38 | D |
| 10 | 38.18 | S |
| 11 | 22.56 | T |
| 12 | 26.06 | T |
| 13 | 46.84 | D |
| 14 | 50.40 | S |
| 15 | 32.67 | T |
| 16 | 29.59 | T |
| 17 | 49.61 | D |
| 18 | 28.42 | Q |
| 19 | 16.81 | Q |
| 20 | 16.24 | Q |
| 21 | 16.90 | Q |
| 22 | 16.38 | Q |
| 1' | 58.97 | T |
| 2' | 144.39 | S |
| 3' | 127.78 | D |
| 4' | 30.95 | T |
| 5' | 78.72 | D |
| 6' | 73.87 | S |
| 7' | a 26.02 | Q |
| 8' | a 24.78 | Q |
| 1" | 105.35 | D |
| 2" | 80.91 | D |
| 3" | b 78.38 | D |
| 4" | 71.52 | D |
| 5" | 76.95 | D |
| 6" | 70.11 | T |
| 1''' | 104.51 | D |
| 2''' | 76.35 | D |
| 3''' | b 78.39 | D |
| 4''' | 72.00 | D |
| 5''' | b 78.12 | D |
| 6''' | 63.19 | T |
| 1'''' | 104.93 | D |
| 2'''' | 75.25 | D |
| 3'''' | b 78.08 | D |
| 4'''' | 71.74 | D |
| 5'''' | b 77.94 | D |
| 6'''' | 62.87 | T |

Application Example 1

Sensory Evaluation of Balansin A and Balansin B

A group of experts tasted and sensorily evaluated the two isolated compounds Balansin A and Balansin B from Example 4, each at a concentration of 50 ppm in water and a 5 wt % aqueous saccharose solution.

Balansin A in the aqueous solution was described as intensely sweet, also as slightly bitter and displayed a sweetener-type note.

Balansin B was described as slightly bitter, slightly sweetener-type and weakly ethanolic, but otherwise displayed no noticeable intrinsic taste.

Application Example 2

Intrinsic Sweetness of Balansin A

In order to evaluate the intrinsic sweetness of the sweet-tasting compound Balansin A, different concentrations of Balansin A were tasted against a saccharose reference series (10 different concentrations in increasing sequence). This reference series consisted of samples in the following concentrations: 0; 0.25; 0.5; 0.75; 1; 1.5; 2; 3; 4 and 5 wt % saccharose in water.

Figure 2:
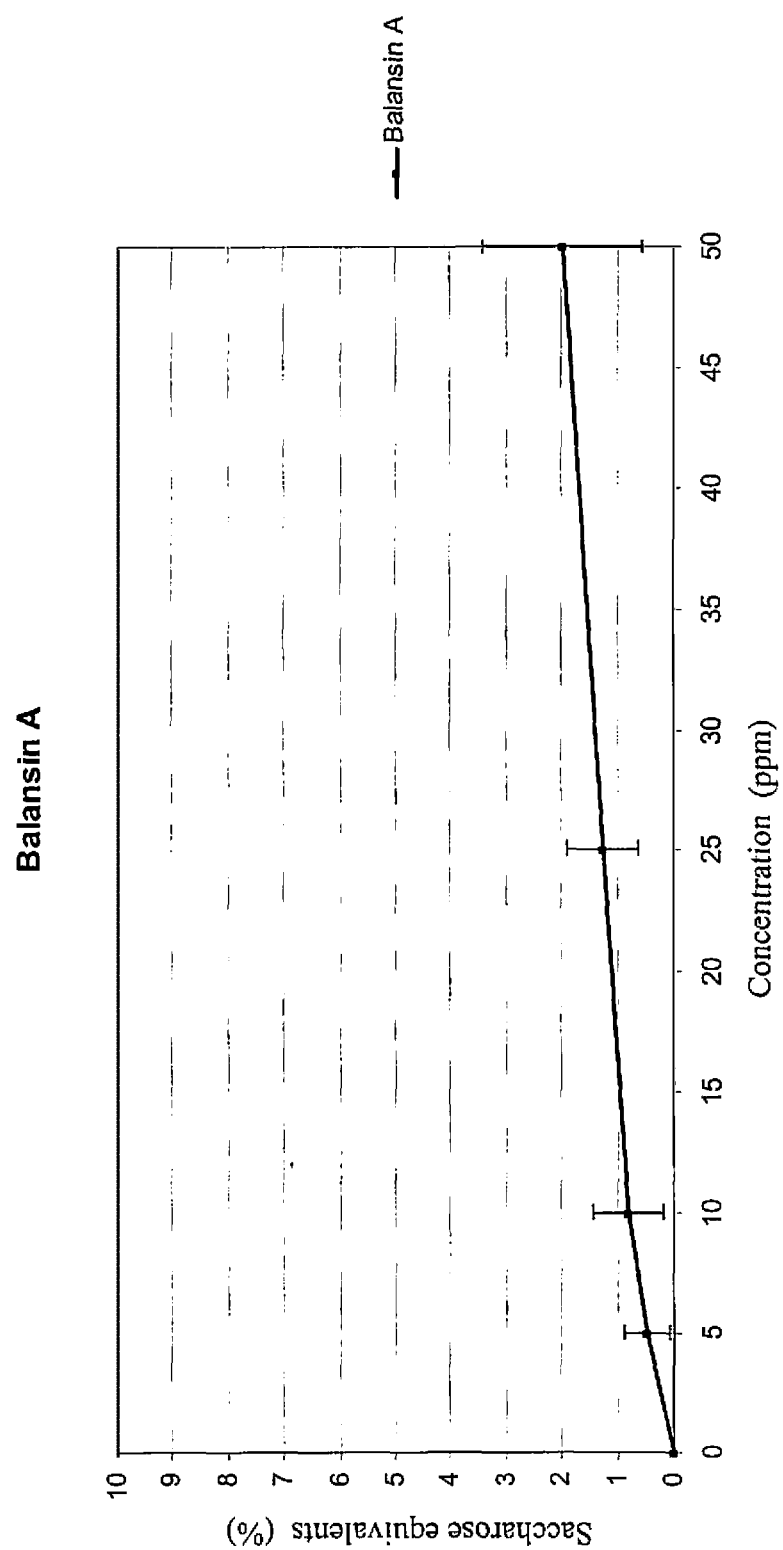
FIG. 2 is a graph illustrating intrinsic sweetness of Balansin A.

FIG. 2 illustrates the intrinsic sweetness of Balansin A at concentrations of 5, 10, 25 and 50 ppm (plotted on the abscissa) compared to a saccharose reference series. The abscissa indicates the concentration of Balansin A in ppm, the ordinates the saccharose equivalents.

Figure 3:
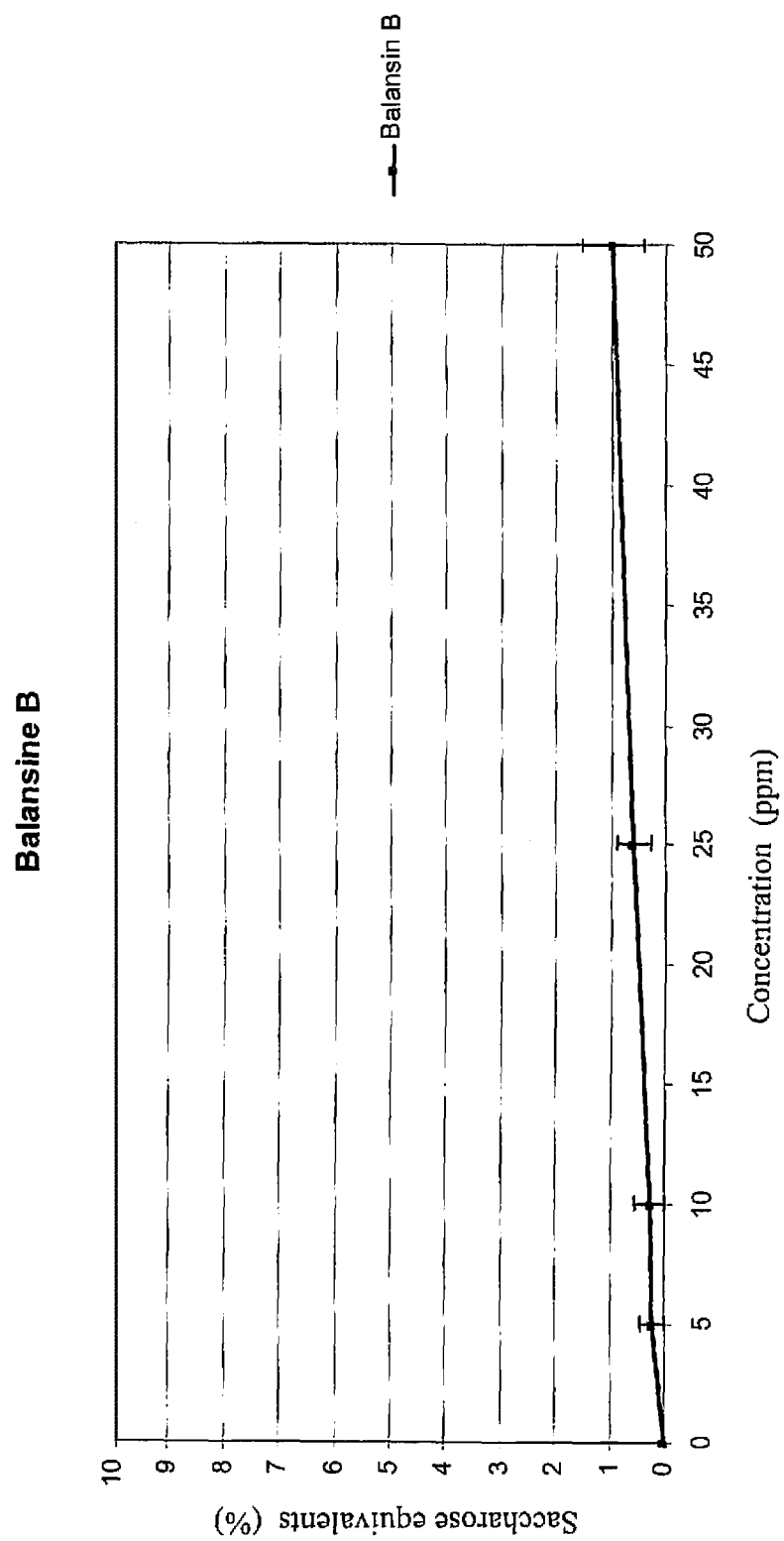
FIG. 3 is a graph illustrating intrinsic sweetness of Balansin B.

FIG. 3 illustrates the intrinsic sweetness of Balansin B at concentrations of 5, 10, 25 and 50 ppm (plotted on the abscissa) compared to a saccharose reference series. The abscissa indicates the concentration of Balansin A in ppm, the ordinates the saccharose equivalents.

It can be seen from FIGS. 2 and 3 that both Balansin A and Balansin B have a certain intrinsic sweetness. At a concentration of 50 ppm, the intrinsic sweetness of Balansin A is equivalent to the sweetness of 2% saccharose, and the intrinsic sweetness of Balansin B is equivalent to the sweetness of 1% saccharose.

Application Example 3

Reinforcing the Sweet Impression of a Sugar Solution

In order to quantify the reinforcement of the sweet impression, the sweetness of a 5 wt %-containing saccharose solution and of a sample which contained 5 wt % saccharose and a quantity of the test substance or test extract was determined by a group of experts (rating 1 [not sweet] to 10 [extremely sweet]). The analysis was performed as a calculation of the reduction (in %) of the sweet impression from the average values of the assessments of the saccharose solution and of the solution containing saccharose and Compound 2 (p was determined as a significance measure according to the paired, two-tailed Student's statistical test).

| Substance/extract | Sweet impression (1-10) without | with | % Reinforcement of the sweet impression |
|---|---|---|---|
| Balansin A, 25 ppm | 4.9 ± 1.5 | 7.2 ± 1.4 | 48% ($p < 0.00005$) |
| Balansin B, 50 ppm | 5.1 ± 1.1 | 6.7 ± 1.1 | 31% ($p < 0.0005$) |
| *Mycetia balansae* extract, 550 ppm (equivalent to 25 ppm Balansin A) | 4.8 ± 1.2 | 7.1 ± 2.4 | 46.6% ($p < 0.001$) |

Application Example 4

Sugar-Reduced Soft Drink, Lemon Type

Formulation A: Comparator formulation with 10 wt % sugar

Formulation B: Comparator formulation with 8 wt % sugar

Formulation C-I: sugar-reduced formulations according to the invention with 8 wt % sugar

| Constituent Formulation | A | B | C | D | E | F | G | H | I |
|---|---|---|---|---|---|---|---|---|---|
| Sugar (saccharose) | 10 | 8 | 8 | 8 | 8 | 8 | 8 | 7 | 0 |
| Citric acid | 0.15 | 0.15 | 0.15 | 0.15 | 0.15 | 0.15 | 0.15 | 0.15 | 0.15 |
| Citrus flavouring | 0.1 | 0.1 | 0.1 | 0.1 | 0.1 | 0.1 | 0.1 | 0.1 | 0.1 |
| Balansin A | — | — | 0.005 | — | 0.0025 | — | 0.001 | 0.001 | 0.010 |
| Balansin B | — | — | — | — | — | 0.002 | — | — | 0.050 |
| Extract of *Mycetia balansae* according to Example 3 | — | — | — | 0.1 | — | — | — | — | — |
| Phloretin | — | — | — | — | — | — | 0.001 | — | — |
| Hesperetin | — | — | — | — | 0.010 | — | — | — | — |
| 3',7-dihydroxy-4'-methoxyflavan according to EP 2 253 226 | — | — | — | — | — | — | — | 0.0025 | — |
| Extract from *Rubus suavissimus*, containing 5 wt% rubusoside based on the total weight of the extract | — | — | — | — | — | 0.010 | — | — | — |
| Extract from extract from *Hydrangea dulcis*, containing 8% phyllodulcin based on the total weight of the extract | — | — | — | — | — | — | — | 0.010 | — |
| Water | | | | | top up to 100 | | | | |

The ingredients were mixed in the indicated sequence and filled up to 100% with water. The mixtures are filled in glass bottles and carbonised.

A sensory assessment of the formulations was carried out by experts. By reducing sugar (20 wt % based on the saccharose quantity), a reduction in sweetness of approx. 36% was observed (formulations B to A). In the formulations C to I, the sweet taste could not be differentiated from the whole sugar formulation A.

Application Example 5

Semi-Finished Products (Flavour Compositions) Containing Natural Sweeteners

| Constituent | A | B | C | D | E | F | G | H |
|---|---|---|---|---|---|---|---|---|
| "Liquid sugar", contains 80% saccharose | 99.9 | — | — | — | — | — | 99.85 | — |
| Rebaudioside A 98% | — | 85 | — | — | 25 | — | 0.01 | 73.5 |
| Stevioside 95% | — | — | 73 | — | — | — | — | — |
| Balansin A | 0.05 | 10 | — | — | 80 | 10 | 0.02 | 10 |
| Balansin B | — | 5 | 20 | — | — | 10 | — | 10 |
| Extract of *Mycetia balansae* according to Example 3 | — | — | — | 30 | — | — | — | — |
| Extract from *Rubus suavissimus*, containing 5 wt % rubusoside based on the total weight of the extract, e.g. from PlantExtrakt | — | — | — | 25 | — | 25 | 0.07 | — |
| Extract from extract from *Hydrangea dulcis*, containing 8% phyllodulcin based on the total weight of the extract | — | — | — | 25 | — | 25 | — | — |
| Phloretin | 0.02 | — | 4 | 5 | 3.2 | 3.5 | 0.02 | 5 |
| Hesperetin | 0.02 | — | 1 | 5 | 0.8 | 1 | 0.02 | 1 |
| 3',7-dihydroxy-4'-methoxyflavan according to EP 2 253 226 | 0.01 | — | 2 | 8 | — | — | 0.01 | — |
| Neohesperidin dihydrochalcone | — | — | — | — | — | 0.5 | — | — |
| Homoeriodictyol sodium salt | — | — | — | — | 16 | — | — | — |
| Vanillin, natural | — | — | — | 2 | — | — | — | — |
| Sugar distillate from cane sugar (e.g. Treatt) | — | — | — | — | — | — | — | 0.5 |

The constituents are mixed in the above-indicated proportions and can then be (further) used in this form. The typical dosage of the formulations A and G in the finished product is in the range of 7 to 15 wt % based on the total weight of the finished product. The typical dosage of the remaining formulations in application example 5 is in the range of 0.01 to 0.1 wt %, preferably 0.03 to 0.06 wt %, based on the total weight of the finished product.

Application Example 6

Mixtures and Semi-Finished Products According to the Invention

| Constituent | A | B | C | D | E | F | G | H |
|---|---|---|---|---|---|---|---|---|
| Balansin A | 80 | 20 | 50 | 50 | 20 | 40 | 20 | 20 |
| Balansin B | 20 | 80 | | | | | | 20 |
| Rebaudioside A 98% | | | 50 | 25 | | | | 20 |
| Stevioside 95% | | | | 25 | | | | |
| Saccharin ® sodium salt | | | | | 20 | | | |
| Cyclamate ® | | | | | | 75 | | |
| Acesulfame ® K | | | | | 20 | | | |
| Aspartame ® | | | | | 20 | | | |
| Neotame ® | | | | | | 5 | | |
| Thaumatin | | | | | | | | 20 |
| Sucralose ® | | | | | | | 80 | |
| Glycyrrhizin ammonium salt | | | | | | | | 20 |

The constituents are mixed in the above-indicated proportions and used for sweetening orally consumable formulations. The typical dosage of mixtures A to H in the finished product is in the range of 0.001 to 0.5 wt %, preferably in the range of 0.003 to 0.1 wt %, based on the total weight of the finished product.

Application Example 7

Semi-Finished Products (with Non-Calorific Sugars and/or Sugar Alcohols)

| Constituent | A | B | C | D | E | F | G | H |
|---|---|---|---|---|---|---|---|---|
| Mixture A from Application example 6 | | | 0.05 | | | 0.05 | | 0.05 |
| Mixture C from Application example 6 | | | | 0.05 | | | 0.05 | |
| Mixture H from Application example 6 | | | | | 0.05 | | | 0.05 |
| Balansin A | 0.05 | | | | | | | |
| Maltite | 50 | 10 | | | | | | |
| Mannite | | 10 | | | | | | |
| Sorbitol | 20 | 20 | | | | | | |
| Erythritol | 29.95 | 59.95 | 99.95 | 99.95 | | 50 | 50 | 99.95 |
| Xylitol | | | | | | | 49.95 | |
| Palatinose | | | | | 50 | | | |
| Tagatose | | | | | 49.95 | 49.95 | | |

The substances are mixed in the above-indicated proportions and used for sweetening orally consumable formulations. The typical dosage of semi-finished products A to H in the finished product is in the range of 0.01 to 80 wt %, preferably is in the range of 0.1 to 50 wt %, particularly preferably is in the range of 0.1 to 10 wt %, in each case based on the total weight of the finished product. The semi-finished products A to H can be used as a sweetener, e.g., also directly in coffee or tea.

Application Example 8

Spray-Dried Formulation as Semi-Finished Product for Flavouring Finished Products

| | Use in wt % Formulation | | | | |
|---|---|---|---|---|---|
| Constituent | A | B | C | D | E |
| Drinking water | 60.8 | 60.8 | 60.8 | 60.8 | 60.8 |
| Maltodextrin from wheat | 24.3 | 24.3 | 24.3 | 24.3 | 24.3 |
| Gum arabic | 6.1 | 6.1 | 6.1 | 6.1 | 6.1 |
| Balansin A | 8.8 | 3.3 | 4.0 | — | — |
| Balansin B | — | 3.3 | 1.5 | 3.3 | 4.4 |
| Hesperetin | — | 2.2 | — | — | 1.1 |
| Homoeriodictyol sodium salt | — | — | — | 5.5 | 3.3 |
| Phloretin | — | — | 3.3 | — | — |

The drinking water is provided in a container and the maltodextrin and gum arabic dissolved therein. Then the flavourings are emulsified in the carrier solution using a Turrax. The temperature of the spray solution should not exceed 30° C. The mixture is then spray-dried (inlet target temperature: 185-195° C., outlet target temperature: 70-75° C.).

Application Example 9

Solutions of Semi-Finished Products

The mixtures and semi-finished products from the above application examples 5, 6 and 7 can also be taken up with water, propylene glycol, glycerine or ethanol or preferably with mixtures of the aforesaid solvents (e.g. water-propylene glycol, water-glycerine, water-ethanol, glycerine-ethanol, glycerine-propylene glycol, propylene glycol-ethanol), for example, as 1-20% solution, preferably 2-10%, particularly preferably 5% solution, and completely dissolved through gentle heating.

Application Example 10

"Cola" Type Soft Drink

| | Formulation (use in wt %) | | | | | | |
|---|---|---|---|---|---|---|---|
| Constituent | A | B | C | D | E | F | G |
| Saccharose | 0 | 8 | 7 | 7 | — | 7 | — |
| Glucose/fructose syrup from maize, containing 55 wt % fructose | — | — | — | — | 8 | — | 7 |
| Flavouring composition A from Application example 5 | 10 | — | — | — | — | — | — |
| Flavouring composition B from Application example 5 | — | 0.05 | — | — | — | — | — |
| Flavouring composition C from Application example 5 | — | — | 0.05 | — | — | — | — |
| Flavouring composition D from Application example 5 | — | — | — | 0.05 | — | — | — |
| Flavouring composition E from Application example 5 | — | — | — | — | 0.05 | — | — |
| Flavouring composition F from Application example 5 | — | — | — | — | — | 0.05 | — |
| Flavouring composition H from Application example 5 | — | — | — | — | — | — | 0.05 |
| Phosphoric acid | 0.07 | 0.07 | 0.07 | 0.07 | 0.07 | 0.07 | 0.07 |
| Citric acid | 0.06 | 0.06 | 0.06 | 0.06 | 0.06 | 0.06 | 0.06 |
| Caramel colouring | 0.14 | 0.14 | 0.14 | 0.14 | 0.14 | 0.14 | 0.14 |
| Caffeine | 0.01 | 0.01 | 0.01 | 0.01 | 0.01 | 0.01 | 0.01 |
| "Cola" type drink emulsion | 0.05 | 0.05 | 0.05 | 0.05 | 0.05 | 0.05 | 0.05 |
| Water | top up to 100% | | | | | | |

The ingredients were mixed in the indicated sequence, bottled and carbonised.

Application Example 11

Sugar-Reduced "Cola" Type Soft Drink

Formulation A: Comparator formulation with 10 wt % sugar
Formulation B: Comparator formulation with 8 wt % sugar
Formulation C-I: sugar-reduced formulations according to the invention with 8 wt % sugar

| | Formulation (use in wt %) | | | | | | |
|---|---|---|---|---|---|---|---|
| Constituent | A | B | C | D | E | F | G |
| Saccharose | 0 | 8 | 8 | 8 | — | — | — |
| Glucose/fructose syrup from maize, containing 55 wt % fructose | — | — | — | — | 8 | 8 | 8 |
| Balansin A | 0.005 | — | 0.003 | 0.0025 | — | 0.003 | 0.0025 |
| Balansin B | — | 0.005 | — | 0.0025 | 0.005 | — | 0.0025 |
| Phosphoric acid | 0.07 | 0.07 | 0.07 | 0.07 | 0.07 | 0.07 | 0.07 |
| Citric acid | 0.06 | 0.06 | 0.06 | 0.06 | 0.06 | 0.06 | 0.06 |
| Caramel colouring | 0.14 | 0.14 | 0.14 | 0.14 | 0.14 | 0.14 | 0.14 |
| Caffeine | 0.01 | 0.01 | 0.01 | 0.01 | 0.01 | 0.01 | 0.01 |
| "Cola" type drink emulsion | 0.05 | 0.05 | 0.05 | 0.05 | 0.05 | 0.05 | 0.05 |
| Water | top up to 100% | | | | | | |

The ingredients were mixed in the indicated sequence and filled up to 100% with water. The mixtures are filled in glass bottles and carbonised.

Application Example 12

Chewing Gum

| Part | Constituent | Use in wt % |
|---|---|---|
| A | Chewing gum base, "Jagum T" Company | 30.95 |
| B | Sorbitol, pulverised | 39.00 |
|  | Isomalt ® (Palatinit GmbH) | 9.50 |
|  | Xylitol | 2.00 |
|  | Mannite | 3.00 |
|  | Aspartame ® | 0.10 |
|  | Acesulfame ® K | 0.10 |
|  | Emulgum ® (Colloides Naturels, Inc.) | 0.30 |
| C | Sorbitol, 70% | 14.00 |
|  | Glycerine | 1.00 |
| D | Balansin A | 0.05 |

Parts A to D are mixed and intensively kneaded. The raw mass can be processed, e.g. in the shape of thin strips into ready-to-consume chewing gums.

Application Example 13

Toothpaste

| Part | Constituent | Use in wt % |
|---|---|---|
| A | Demineralised water | 23.08 |
|  | Sorbitol (70%) | 45.00 |
|  | Solbrol ® M, sodium salt (Bayer AG, p-hydroxybenzoic acid alkyl ester) | 0.15 |
|  | Trisodium phosphate | 0.10 |
|  | Balansin A | 0.02 |
|  | Sodium monofluorophosphate | 1.12 |
|  | Polyethylene glycol 1500 | 5.00 |
| B | Sident 9 (abrasive silicon dioxide) | 10.00 |
|  | Sident 22 S (thickening silicon dioxide) | 8.00 |
|  | Sodium carboxymethyl cellulose | 0.90 |
|  | Titanium dioxide | 0.50 |
| C | Demineralised water | 4.53 |
|  | Sodium lauryl sulfate | 1.50 |
| D | Peppermint flavouring | 0.1 |

The constituents of parts A and B are each separately pre-mixed and thoroughly stirred together under vacuum at 25-30° C. for 30 min. Part C is pre-mixed and added to A and B; D is added and the mixture thoroughly stirred under vacuum at 25-30° C. for 30 min. After relaxation, the toothpaste is ready and can be decanted.

Application Example 14

Sugar-Free Hard-Boiled Candy

| | Content (data in wt %) | | | |
|---|---|---|---|---|
| Constituent | A | B | C | D |
| Palatinite, type M | 75.00 | 74.00 | 75.50 | 75.00 |
| Citric acid | — | 1.0 | 0.5 | — |
| Water | 24.88 | 24.842 | 23.87 | 24.8815 |
| Yellow colouring | — | 0.01 | — | — |
| Red colouring | — | — | 0.01 | — |
| Blue colouring | 0.01 | — | — | 0.01 |
| Peppermint flavouring | 0.1 | — | — | 0.1 |
| Citrus flavouring | — | 0.1 | — | — |
| Red fruit flavouring | — | — | 0.1 | — |
| Rebaudioside A 98% | — | 0.040 | — | — |
| Balansin A | 0.010 | 0.005 | 0.020 | 0.005 |
| Hesperetin | — | 0.001 | — | 0.001 |
| Phloretin | — | 0.002 | — | — |
| 3',7-dihydroxy-4'-methoxyflavan according to EP 2 253 226 | — | — | — | 0.0025 |

Palatinite was mixed with water, if necessary, after adding citric acid, and the mixture melted at 165° C. and then cooled to 115° C. The flavouring and the other ingredients were added and, after stirring thoroughly, poured into moulds, removed from the moulds after hardening and then individually packed.

Application Example 15

Sugar-Reduced Blancmange-Type Pudding

The formulations A and B are comparator formulations with full (formulation A) and reduced sugar content (formulation B)

| | Formulation (data in wt %) | | | | | |
|---|---|---|---|---|---|---|
| Constituent | A | B | C | D | E | F |
| Saccharose | 7.8% | 5.4% | 5.4% | 5.4% | 5.4% | 5.4% |
| Starch | 3.0% | 3.0% | 3.0% | 3.0% | 3.0% | 3.0% |
| Skimmed milk powder | 1.5% | 1.5% | 1.5% | 1.5% | 1.5% | 1.5% |
| Aubygel MR50 | 0.5% | 0.5% | 0.5% | 0.5% | 0.5% | 0.5% |
| Balansin A | — | — | 0.01% | 0.005% | 0.005% | 0.005% |
| Extract (e.g. from PlantExtrakt) from *Rubus suavissimus*, containing 5 wt % rubusoside based on the total weight of the extract | — | — | — | — | 0.010% | 0.005% |
| Hesperetin | — | — | — | 0.001% | — | 0.001% |
| Phloretin | — | — | — | 0.002% | — | 0.001% |
| 3',7-dihydroxy-4'-methoxyflavan according to EP 2 253 226 | — | — | — | — | — | 0.001% |
| Vanilla pod extract, spray-dried, Symrise | 0.1% | 0.1% | 0.1% | 0.1% | 0.1% | 0.1% |
| Milk 1.5% fat content | top up to 100% | | | | | |

The solid substances were provided and stirred with the milk. The mixture was heated up to 95° C. for 2 min while being stirred thoroughly, decanted and cooled down to 5-8° C.

Application Example 16

Low-Fat Yoghurts

Formulation A with sugar is a comparator formulation.
Formulations according to the invention with sweetener mixture and extract from example 2) (B-D)

| Constituent | Formulation (data in wt %) | | | |
|---|---|---|---|---|
| | A | B | C | D |
| Saccharose | 10 | 8 | 6 | — |
| Strawberry fruit formulation | 10 | 10 | 10 | 10 |
| Rebaudioside A 98% | — | — | — | 0.050 |
| Balansin A | — | 0.010 | 0.005 | 0.010 |
| Extract from *Rubus suavissimus* (e.g. from PlantExtrakt) containing 5 wt % rubusoside based on the total weight of the extract | — | — | 0.010 | — |
| Hesperetin | — | 0.001 | 0.001 | 0.001 |
| Phloretin | — | — | 0.002 | — |
| Hopmoeriodictyol sodium salt | — | — | — | 0.005 |
| Natural strawberry flavouring | 0.1% | 0.1% | 0.1% | 0.1% |
| Yoghurt, 0.1% fat | top up to 100% | | | |

The constituents were mixed and cooled at 5° C.

Application Example 17

Milk Mix Drinks

Formulation A is a comparator formulation with sugar
Formulations B to D are formulations according to the invention

| Constituent | Formulation (data in wt %) | | | |
|---|---|---|---|---|
| | A | B | C | D |
| Saccharose | 10 | 8 | 7 | — |
| Fructose | — | — | 0.5 | — |
| Rebaudioside A 98% | — | — | — | 0.040 |
| Balansin A | — | 0.010 | 0.005 | 0.010 |
| Extract from *Rubus suavissimus* (e.g. from PlantExtrakt), containing 5 wt % rubusoside based on the total weight of the extract, | — | — | 0.010 | — |
| Hesperetin | — | 0.003 | 0.002 | 0.005 |
| Phloretin | — | — | 0.002 | — |
| Homoeriodictyol sodium salt | — | — | — | 0.002 |
| Vanilla flavouring | 0.1 | 0.1 | 0.1 | 0.1 |
| Long-life milk, 1.5% fat | top up to 100% | | | |

The constituents were mixed, topped up with milk, stirred thoroughly, bottled and refrigerated at 5° C.

Application Example 18

Sugar-Reduced Tomato Ketchup

Comparator formulation with sugar (A)
Comparator formulation with reduced sugar content (B)
Formulations (C-I) according to the invention

| Constituent | Formulation (data in wt %) | | | | | | | |
|---|---|---|---|---|---|---|---|---|
| | A | B | C | E | F | G | H | I |
| Cooking salt | 2 | 2 | 2 | 2 | 2 | 2 | 2 | 2 |
| Starch, Farinex WM 55 | 1 | 1 | 1 | 1 | 1 | 1 | 1 | 1 |
| Saccharose | 12 | 9.6 | 9.2 | 8.4 | 9.6 | 9.6 | 8.4 | 4.2 |
| Double-concentrated tomato puree | 40 | 40 | 40 | 40 | 30 | 30 | 30 | 30 |
| Glucose syrup 80 Brix | 18 | 18 | 18 | 18 | 18 | 18 | 18 | 18 |
| Spirit vinegar 10% | 7 | 7 | 7 | 7 | 3 | 3 | 3 | 3 |
| Rebaudioside A 98% | — | — | — | — | — | — | — | 0.05 |
| Balansin A | — | — | 0.01 | 0.005 | 0.005 | 0.01 | 0.005 | 0.01 |
| Extract from *Rubus suavissimus* (e.g. from PlantExtrakt) containing 5 wt % rubusoside based on the total weight of the extract | — | — | — | — | — | — | 0.01 | — |
| Hesperetin 2.5% in 1,2-propylene glycol | — | — | — | — | 0.1 | — | 0.1 | — |
| Phloretin 2.5% in 1,2-propylene glycol | — | — | — | 0.2 | 0.2 | — | — | 0.3 |
| Water | top up to 100% | | | | | | | |

The substances are mixed in the given sequence and the finished ketchup is homogenised with the aid of a mixer, bottled and sterilised.

Application Example 19

Sugar-Reduced Ice-Cream

Comparator formulation with sugar (A)
Comparator formulation with reduced sugar content (B)
Formulations (C-F) according to the invention

| Constituent | Formulation (content in wt %) | | | | | |
|---|---|---|---|---|---|---|
| | A | B | C | D | E | F |
| Vegetable fat, melting range 35-40° C. | 20.00 | 20.00 | 20.00 | 20.00 | 20.00 | 20.00 |
| Sugar (saccharose) | 12.00 | 8.00 | 8.00 | 8.00 | 8.00 | 8.00 |
| Skimmed milk powder | 5.00 | 5.00 | 5.00 | 5.00 | 5.00 | 5.00 |
| Glucose syrup 72% dry matter | 5.00 | 5.00 | 5.00 | 5.00 | 5.00 | 5.00 |

-continued

| Constituent | Formulation (content in wt %) | | | | | |
|---|---|---|---|---|---|---|
| | A | B | C | D | E | F |
| Emulsifier SE 30 (Grindstedt Products, Denmark) | 0.65 | 0.65 | 0.65 | 0.65 | 0.65 | 0.65 |
| Flavouring containing 0.1% diacetyl and 1% vanillin | 0.20 | 0.20 | 0.20 | 0.20 | 0.20 | 0.20 |
| Balansin A | — | — | 0.01 | 0.005 | 0.01 | 0.005 |
| Extract from Rubus suavissimus (e.g. from PlantExtrakt), containing 5 wt % rubusoside based on the total weight of the extract, | — | — | — | — | — | 0.010 |
| Hesperetin 2.5% in 1,2-propylene glycol | — | — | — | 0.10 | — | 0.10 |
| Phloretin 2.5% in 1,2-propylene glycol | — | — | — | — | 0.05 | 0.05 |
| Skimmed milk | top up to 100% | | | | | |

The vegetable fat was heated to 58° C. Skimmed milk and glucose syrup were heated to 55° C. and sugar, skimmed milk powder, emulsifier and flavouring added, and the mixture added to the vegetable fat. The mixture was homogenised with the aid of a through-flow high-pressure homogeniser (180/50 bar). The mass obtained was tempered for 1 min at 78° C., then cooled to 2-4° C., and incubated at this temperature for 10 h until matured. Then, the matured mass was decanted and stored in the freezer at −18° C.

Application Example 20

Ice-Cream Suitable for Diabetics

An ice-cream suitable for diabetics was produced from the following ingredients and filled in tubs in portions of 95 mL each:
condensed skimmed milk, fructose syrup, strawberry pieces and strawberry puree (15 wt %), vegetable fat, diabetic chocolate flakes (3.5 wt %, with emulsifier soya lecithin), whey product, beetroot juice, locust bean gum, guar gum, carrageen, emulsifier (E 471), gelatine, acidifier, citric acid, 0.1 wt % strawberry flavouring (containing 1 wt % Balansin A, based on the total weight of the strawberry flavouring), colouring carotene.
Calorific value (per 95 mL):
protein 1.8 g, carbohydrates 13.3 g (of which fructose 9.5 g), fat 4.2 g.

Application Example 21

Diabetic Chocolate Based on Maltite

Chocolate suitable for diabetics was produced from the following ingredients and poured into rectangular bars:
maltite, hazelnut mass, cocoa butter, skimmed milk powder, cocoa mass, inulin, clarified butter, emulsifier soya lecithins, 0.1 wt % vanilla flavouring (containing vanilla pod extract, vanillin and 5 wt % Balansin A, based on the total weight of the vanilla flavouring).
Calorific value (per 100 g):
protein 8 g, carbohydrates 43 g (of which maltite 34 g), fat 34 g.

Application Example 22

Diabetic Chocolate Based on Fructose

Chocolate suitable for diabetics was produced from the following ingredients and poured into rectangular bars:
cocoa mass, fructose, skimmed milk powder, cocoa butter, inulin, clarified butter, emulsifier soya lecithins, walnuts, table salt, 0.1 wt % vanilla flavouring (containing vanillin and 1 wt % Balansin A from Example 2, based on the total weight of the vanilla flavouring).
Calorific value (per 100 g):
protein 8.8 g, carbohydrates 34 g (of which fructose 23 g, lactose 7.5 g, saccharose 1.4 g), fat 36 g; dietary fibre 18.5 (of which 12.2 g inulin); sodium: 0.10 g. Cocoa content minimum 50 wt %.

Application Example 23

Sugar-Reduced Muesli Mixture

| No. | | A (wt %) | B (wt %) |
|---|---|---|---|
| 1 | Oat flakes | 17.00 | 18.90 |
| 2 | Crispy oat flake clusters | 10.00 | 12.00 |
| 3 | Rice crispies | 16.90 | 17.80 |
| 4 | Cornflakes | 16.50 | 17.50 |
| 5 | Currants | 3.50 | 3.50 |
| 6 | Hazelnuts, chopped | 2.50 | 2.50 |
| 7 | Glucose syrup from wheat, DE 30 | 9.50 | 9.50 |
| 8 | Saccharose | 20.00 | 14.00 |
| 9 | Water | 4.00 | 4.00 |
| 10 | Citric acid powder, anhydrous | 0.10 | 0.10 |
| 11 | Flavouring composition D from Application Example 5 | — | 0.20 |

Mix each of ingredients no. 1 to 6 in a rotary drum (Mix 1). Heat up each of ingredients no. 7 to 9 and add ingredient no. 10 (and in the formulation B add ingredient no. 11 as well) (Mix 2). Add Mix 2 to Mix 1 each time and mix thoroughly. Finally, put the resulting muesli mixture on a baking sheet and dry in an oven at 130° C. for 8 minutes.

Application Example 24

Sugar-Reduced Fruit Gums

| | A (wt %) | B (wt %) |
|---|---|---|
| Water | 23.70 | 25.70 |
| Saccharose | 34.50 | 8.20 |
| Glucose syrup, DE 40 | 31.89 | 30.09 |
| Iso Syrup C* Tru Sweet 01750 (Cerestar GmbH) | 1.50 | 2.10 |

-continued

|  | A (wt %) | B (wt %) |
|---|---|---|
| Gelatine 240 Bloom | 8.20 | 9.40 |
| Polydextrose (Litesse ® Ultra, Danisco Cultor GmbH) | — | 24.40 |
| Yellow and red colouring | 0.01 | 0.01 |
| Citric acid | 0.20 |  |
| Cherry flavouring, containing 1 wt % Balansin A and 0.3 wt % phloretin, based on the cherry flavouring | — | 0.10 |

Polydextrose is a polysaccharide with low calorific value which does not itself taste sweet.

Application Example 25

Chocolate-Cappuccino Ice-Cream

|  | A (wt %) | B (wt %) |
|---|---|---|
| Glucose-fructose syrup | 14.30 | 14.30 |
| Saccharose | 10.00 | 7.50 |
| Skimmed milk powder | 5.00 | 5.00 |
| Cream (36% fat content) | 24.00 | 24.00 |
| Emulsifier and stabiliser Cremodan 709VEG (Danisco) | 0.50 | 0.50 |
| Cocoa powder | 5.975 | 5.975 |
| Carrageenan | 0.025 | 0.025 |
| Water | 40.20 | 42.50 |
| Cappuccino flavouring containing 1 wt % Balansin B and 1 wt % homoeriodictyol sodium salt, based on the flavouring | — | 0.20 |

The invention claimed is:

1. A plant comprising one or a plurality of compounds selected from at least one of the following formulas I, II, or III:

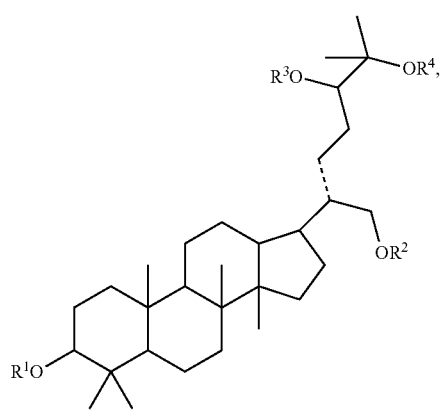

where the dotted line represents a single or a double bond, and $R^1$, $R^2$, $R^3$ and $R^4$ each independently of each other represent hydrogen or sugar residue,

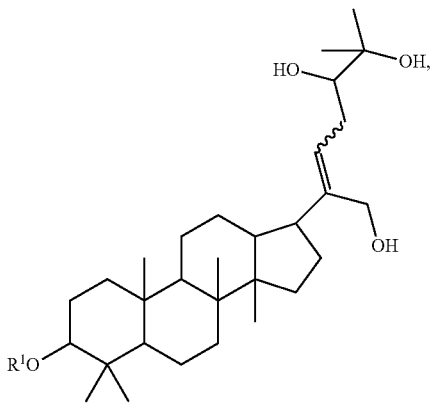

wherein $R^1$ is a mono-, di-, tri-, tetra- or pentasaccharide residue,

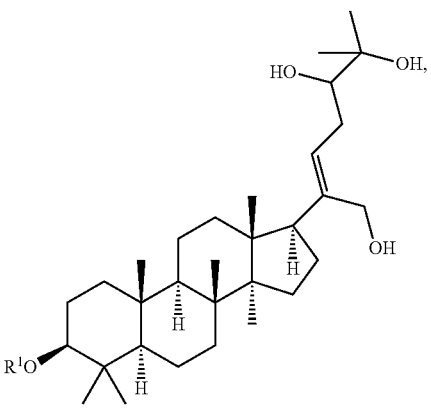

wherein $R^1$ is a mono-, di-, tri-, tetra- or pentasaccharide residue selected from the group consisting of
(b-i) glucosyl, mannosyl, galactosyl, rhamnosyl, fucosyl, arabinosyl, ribosyl and mixtures thereof, and
(b-ii) the oligosaccharide residues of 2 to 5 simple sugar building blocks, said simple sugar building blocks being selected from the group consisting of glucose, mannose, galactose, rhamnose, fucose, arabinose, ribose and mixtures thereof,
and mixtures of (b-i) and (b-ii) wherein
the total amount of these compounds is in the range of 0.0005 to 80 wt, based on the dry mass of the extract, obtained by a method comprising the following step or steps:
a) single or multiple extraction of plant material from *Mycetia balansae* with a liquid extractant of water and ethanol in 1:4 volume:volume ratio,
and, optionally, one or a plurality of further steps as follows:
b) concentrating the primary extract obtained in Step a),
c) treating the primary extract obtained in Step b) with or on adsorbents selected from the group consisting of silica gel, modified silica gel, activated carbon, zeolite, bentonite, diatomaceous earth, aluminium oxide, ion exchangers and mixtures thereof, to obtain a purified secondary extract,
d) drying the secondary extract obtained in Step c),
e) mixing the dried secondary extract obtained in Step d) with a diluent or with a mixture of two or a plurality of diluents selected from the group consisting of ethanol, isopropanol, 1,2-propylene glycol, vegetable oil triglycerides, diacetin, triacetin, glycerine and mixtures thereof, to obtain a solution.

2. An orally consumable formulation, comprising a sensorily active amount of the plant extract of claim 1, wherein the orally consumable formulation is selected from the group consisting of alimentary formulations, dietary supplement formulations, stimulant formulations, oral pharmaceutical formulations, mouth care products, flavouring compositions, cosmetic formulations and mixtures thereof.

3. The orally consumable formulation according to claim 2, additionally comprising one, two, three, four, five, six, seven, eight, nine, ten or a plurality of further substances, selected from the following groups (a1) to (a5):
- (a1) one, two, three, four, five or a plurality of flavourings being selected from the group consisting of: vanillin, ethyl vanillin, 2-hydroxy-4-methoxybenzaldehyde, ethyl vanillin isobutyrate (=3 ethoxy-4-isobutyryloxybenzaldehyde), (2,5-dimethyl-4-hydroxy-3(2H)-furanone) and derivatives, homofuronol (2-ethyl-5-methyl-4-hydroxy-3(2H)-furanone and 5-ethyl-2-methyl-4-hydroxy-3(2H)-furanone), maltol and its derivatives, coumarin and its derivatives, gamma-lactones, delta-lactones, methyl sorbate, divanillin, 4-hydroxy-2(or 5)-ethyl-5(or 2)-methyl-3(2H)furanone, 2-hydroxy-3-methyl-2-cyclopentenone, 3-hydroxy-4,5-dimethyl-2(5H)-furanone, fruit esters and fruit lactones, 4-(p-hydroxyphenyl)-2-butanone, 1,1-dimethoxy-2,2,5-trimethyl-4-hexane, 2,6-dimethyl-5-hepten-1-al, phenylacetaldehyde and mixtures thereof;
- (a2) carbohydrates selected from the group consisting of saccharose, trehalose, lactose, maltose, melizitose, melibiose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde, maltodextrins and mixtures thereof and plant formulations containing one or a plurality of the cited carbohydrates, honey, invert sugar syrup or highly enriched fructose syrup from maize starch;
- (a3) sugar alcohols selected from the group consisting of glycerine, erythritol, threitol, arabitol, ribitol, xylitol, sorbitol, mannitol, maltitol, isomalt, dulcitol, lactitol and mixtures thereof, and the physiologically acceptable salts of these sugar alcohols;
- (a4) naturally occurring sweeteners selected from the group consisting of
- (a4-1) miraculin, monellin, mabinlin, thaumatin, curculin, brazzein, pentaidin, D-phenylalanine, D-tryptophan, extracts or fractions obtained from natural sources containing these amino acids and/or proteins and mixtures thereof, and the physiologically acceptable salts of these amino acids and/or proteins;
- (a4-2) neohesperidin dihydrochalcone, naringin dihydrochalcone, stevioside, steviolbioside, rebaudiosides, rebaudioside A, rebaudioside B, rebaudioside C, rebaudioside D, rebaudioside E, rebaudioside F, rebaudioside G, rebaudioside H, dulcosides and rubusoside, suavioside A, suavioside B, suavioside G, suavioside H, suavioside I, suavioside J, baiyunoside 1 baiyunoside 2, phlomisoside 1, phlomisoside 2, phlomisoside 3, and phlomisoside 4, abrusoside A, abrusoside B, abrusoside C, abrusoside D, cyclocaryoside A and cyclocaryoside I, osladin, polypodoside A, strogin 1, strogin 2, strogin 4, selligueain A, dihydroquercetin-3-acetate, perillartine, telosmoside $A_{15}$, periandrin I-V, pterocaryosides, cyclocaryosides, mukuroziosides, trans-anethole, trans-cinnamaldehyde, bryosides, bryonosides, bryonodulcosides, camosiflosides, scandenosides, gypenosides, trilobatin, phloridzin, dihydroflavanols, hematoxylin, cyanine, chlorogenic acid, albiziasaponin, telosmosides, gaudichaudioside, mogrosides, mogroside V, hernandulcins, monatin, phyllodulcin, glycyrrhetinic acid, derivatives thereof and mixtures thereof, and the physiologically acceptable salts of these compounds;
- (a4-3) extracts or enriched fractions of extracts selected from the group consisting of Thaumatococcus extracts (katemfe bush), extracts of *Stevia* ssp. (*Stevia rebaudiana*), swingle extracts (*Momordica* or *Siratia grosvenorii*, Luo-Han-Guo), extracts of *Glycerrhyzia* ssp. (*Glycerrhyzia glabra*), extracts of *Rubus* ssp. (*Rubus suavissimus*), citrus extracts, extracts of *Lippia dulcis* and mixtures thereof, and mixtures of any of (a4-1) to (a4-3);
- (a5) synthetically sweet-tasting substances selected from the group consisting of magap, sodium cyclamate or other physiologically acceptable salts of cyclamic acid, acesulfame K or other physiologically acceptable salts, neohesperidin dihydrochalcone, naringin dihydrochalcone, saccharin, saccharin-sodium salt, aspartame, superaspartame, neotame, alitame, advantame, perillartine, sucralose, lugduname, carrelame, sucrononate, sucrooctate and mixtures thereof.

4. The formulation of claim 2, wherein the total amount of extract comprising compounds of the formula (I) is in the range of 0.01 ppm to 95 wt % based on the total mass of the formulation.

5. A method for imparting a sweet taste impression and/or reinforcing a sweet taste impression of one, two or a plurality of sweet-tasting substances and/or producing an orally consumable formulation comprising the following steps:
- a) providing the extract of claim 1,
- b) providing an orally consumable formulation comprising one, two or a plurality of further sweet-tasting substances, and
- c) bringing into contact or mixing of the ingredients provided in Steps a) and b).

6. The method of claim 5, comprising the steps of:
- a-i) producing an extract comprising a compound of formula by extracting plant material from *Mycetia balansae;*
- a-ii) optional further processing of the extract produced in Step (a-i) into a further-processed product comprising a compound of formula I,
- b) providing an orally consumable formulation comprising one, two or a plurality of further sweet-tasting substances,
- c) bringing into contact or mixing the orally consumable formulation from Step b), which comprises one, two or a plurality of further sweet-tasting substances, with the extract produced in Step a-i) and/or the further-processed product produced in Step a-ii).

7. An orally consumable formulation, comprising a sensorily active amount of the plant extract of claim 1, wherein the orally consumable formulation is selected from the group consisting of alimentary formulations, dietary supplement formulations, stimulant formulations, oral pharmaceutical formulations, mouth care products, flavouring compositions, cosmetic formulations and mixtures thereof.

* * * * *